United States Patent [19]
Torczynski et al.

[11] Patent Number: 5,773,579
[45] Date of Patent: Jun. 30, 1998

[54] LUNG CANCER MARKER

[75] Inventors: Richard M. Torczynski, Farmers Branch; Arthur P. Bollon, Dallas, both of Tex.

[73] Assignee: Cytoclonal Pharmaceutics, Inc., Dallas, Tex.

[21] Appl. No.: 776,088

[22] PCT Filed: Jul. 19, 1995

[86] PCT No.: PCT/US95/09145
§ 371 Date: Jan. 21, 1997
§ 102(e) Date: Jan. 21, 1997

[87] PCT Pub. No.: WO96/02552
PCT Pub. Date: Feb. 1, 1996

Related U.S. Application Data

[62] Division of Ser. No. 276,919, filed as PCT/US95/09145 Jul. 19, 1995, Pat. No. 5,589,579.

[51] Int. Cl.$^6$ ............................. C07K 14/00; C07H 21/00
[52] U.S. Cl. ......................... 530/350; 536/23.1; 536/24.3
[58] Field of Search .......................... 530/350; 536/23.1, 536/24.3; 930/10, 240

[56] References Cited

U.S. PATENT DOCUMENTS

| | | | |
|---|---|---|---|
| 4,816,402 | 3/1989 | Rosen et al. | 435/240.27 |
| 4,990,454 | 2/1991 | Yachi et al. | 435/240.27 |
| 5,134,075 | 7/1992 | Hellstrom et al. | 530/387.3 |
| 5,185,432 | 2/1993 | Hellstrom et al. | 530/388.8 |
| 5,200,508 | 4/1993 | Nilaver et al. | 530/350 |

OTHER PUBLICATIONS

Aldred et al., Biochemistry 30(2):569–575 (1991).
Montgomery et al., Genomics 11(14):835–848 (1991).
Anastasi, et al., "Direct correlation of cytogenetic findings with cell morphology using in situ hybridization: an analysis of suspicious cells in bone morrow specimens of two patients completing therapy for acute lymphoblastic leukemia," *Blood* 77:2456–2462 (1991).
Altschul, et al., "Basic local alignment search tool," *J. Molecular Biol* 215:403–410 (1990).
Birrer, et al., "Application of molecular genetics to the early diagnosis and screening of lung cancer," *Cancer Research (supplement)* 52:2658s–2664s (1992).
Boring, et al., "Cancer statistics,1993," *CA Cancer J Clin* 43:7–26 (1993).
Chirgwin, et al., "Isolation of biologically active ribonucleic acid from sources enriched in ribonuclease," *Biochem* 18:5294–5299 (1979).
Diez, et al., "Prognostic significance of serum CA 125 antigen assay in patients with non–small cell lung cancer," *Cancer* 73:1368–1376 (1994).
Flehinger, et al., "The effect of surgical treatment on survival from lung cancer: implications for screening," *Chest* 101:1013–1018 (1992).

Gray, JW and Pinkel, D, "Molecular cytogenetics in human cancer diagnosis," *Cancer (supplement)* 69:1536–1542 (1992).
Hasegawa, et al., "Nonspecific crossreacting antigen (NCA) is a major member of the carcinoembryonic antigen (CEA)–related gene family expressed in lung cancer," *British J Cancer* 67:58–65 (1993).
von Heijne, G., "A new method for predicting signal sequence cleavage sites," *Nucleic Acid Research* 14:4683–4690 (1986).
Kern, et al., "p185$^{neu}$ Expression in human lung adenocarcinomas predicts shortened survival," *Cancer Research* 50:5184–5191 (1990).
Kim, et al., "Interphase cytogenetics in paraffin sections of lung tumors by non–isotopic in situ hybridization," *Am J Path* 142:307–317 (1993).
Kunkel, TA, "Rapid and efficient site–specific mutagenesis without phenotypic selection," *Proc Natl Acad Sci USA* 82:488–492 (1985).
Margolis, et al., "Serum tumor markers in non–small cell lung cancer," *Cancer* 73:605–609 (1994).
Melamed, et al., "Screening for early lung cancer: results of the Memorial Sloan–Kettering study in New York," *Chest* 86:44–53 (1984).
Mitsudomi, et al., "p53 gene mutations in non–small–cell lung cancer cell lines and their correlation with the presence of ras mutations and clinical features," *Oncogene* 7:171–180 (1992).
Mori, et al., "The significance of carbonic anyhdrase expression in human colorectal cancer," *Gastroenterology* 105:820–826 (1993). Abstract Only.
Mulshine, et al., "Section 22.5 Applications of monoclonal antibodies in the treatment of solid tumors," *Biologic Therapy of Cancer*, VT DeVita, S. Hellman, SA Rosenberg (ed), JB Lippencott Co., New York, pp. 563–588 (1991).
Parkin, et al., "Estimates of the worldwide incidence of eighteen major cancers in 1985," *Int J Cancer* 54:594–606 (1993).
Radosevich, et al., "Monoclonal antibody assays for lung cancer," *Cancer Diagnosis In Vitro Using Monoclonal Antibodies*, H. Kupchik (ed.), Marcel Dekker, Inc., New York, pp. 101–121 (1988).

(List continued on next page.)

*Primary Examiner*—W. Gary Jones
*Assistant Examiner*—Ethan Whisenant
*Attorney, Agent, or Firm*—Sidley & Austin

[57] ABSTRACT

The present invention discloses an isolated and purified nucleic acid sequence and corresponding amino acid sequence to a novel protein specific for human lung cancer cells. This gene is expressed at a much higher level in these cells than in normal lung cells, other normal tissues and other tumor cell lines tested. Also disclosed are three additional recombinant forms of this gene and protein, in the first two cases a membrane spanning region is removed and in the third case an amino acid is changed by in vitro mutagenesis.

12 Claims, 1 Drawing Sheet

OTHER PUBLICATIONS

Schepart, BS and Margolis, ML, "Monoclonal antibody–mediated detection of lung cancer antigens in serum," *Am Rev Respir Dis* 138:1434–1438 (1988).

Scott, et al., "Early lung cancer detection using monoclonal antibodies," *Lung Cancer*, JA Roth, JD Cox, and WK Hong (eds), Blackwell Scientific Publications, Boston, pp. 310–323 (1993).

Skonier, et al., "cDNA cloning and sequence analysis of βig–h3, a novel gene induced in a human adenocarcinoma cell line after treatment with transforming growth factor–β," *DNA Cell Biology* 11:511–522 (1992).

Smith, DB and Johnson, KS, "Single–step purification of polypeptides expressed in *Escherichia coli* as fusions with glutathione S–transferase," *Gene* 67:31–40 (1988).

Souhami, et al., "Antigens of lung cancer: results of the Second International Workshop on Lung Cancer Antigens," *J Natl Cancer Institute* 83:609–612 (1991).

Strnad, et al., "Molecular cloning and characterization of a human adenocarcinoma/epithelial cell surface antigen complementary DNA," *Cancer Research* 49:314–317 (1989).

Tockman, et al., "Sensitive and specific monoclonal antibody recognition of human lung cancer antigen on preserved–sputum cells: a new approach to early lung cancer detection," *J Clin Oncology* 6:1685–1693 (1988).

Anon, "Early lung cancer detection: summary and conclusions," *Am Rev Respir Dis* 130:565–570 (1984).

"The World Health Organization histological typing of lung tumours (second edition)," *Am J Clin Path* 77:123–136 (1982).

```
HCAI      ASPDWGYDDKNGPE-QWSKLYPIA-NGN----NQSPVDIKTSETKDTSLKPISVS-YNPATAKE---IIWVGHSFHVNFEDNDN
HCAII     -SHHWGYGKHNGPE-HWHKDFPIA-KGE----RQSPVDIDTHTAKYDPSLKPLSVS-YDQATSLR---ILMNGHAFNVEFDDSQD
HCAIII    -AKEWGYASHNGPD-HWHELFPNA-KGE----NQSPVELHTKDIRHDPSLQPWSVS-YDGGSAKT---ILMNGKTCRVVFDDTYD
HCAIV     AESHWCYEVQAESS-NYPCLVPVRWGGNCQKDRQSPINIVTTKAKVDKKLGRFFSGYDKQTWT--VQMNGHSVMLLEN--K
HCAVI     QHVSDMTYSEGALDEAHPQHYPAC-GGQ----RQSPINLQRTKVRTNPSLKGLMTGYETQAGEFP-MVMNGHTVQIGLPSTMR
HCAVII    GHHGWGYGQ-DDGPSHWHKLYPIA-QG-----DRQSPINIISSQAVISPSLQPLELS-YEACMSLS---ITMNGHSVQVDFNDSDD
HCAV      --CAWQTSNNTLHP-LWTVPVSVP-GGT----RQSPINIQWRDSVYDPQLKPLRVS-YEAASCLY---IWMTGYLPQVEFDDATE
HCAVIII   --SKWTYFPGDGEN-SWSKKYPSC-GGL----LQSPIDLHSDILQYDASLTPLEFQGYNLSANKQFLLTWNGHSVKLNLP-S-D

HCAI      RSVLKGGPFSDSYRLFQFHFHWG---STNEHGSEHTVDGVKYSAELRVAR-WNSAKYSSLAEAASKADGLAVIGVLM--KVG-EA
HCAII     KAVLKGGPLDGTYRLLIQFHFHWG--SLDGQGSEHTVDKKYAAELHLVH-WNT-KYGDFGKAVQQPDGLAVLGIFL--KVG-SA
HCAIII    RSMLRGGPLPGFTRLRQFHLHWG---SSDDHGSEHTVDGVKYAAELHLVH-WNP-KYNTFKEALKQRDGIAVIGIFL--KIG-HE
HCAIV     ASISGGG--LPAPYQAKQLHLHWS--DLPYKGSEHSLDGEHFAMEMHIVHEKEKGTSRNVKEAQDPEDEIAVLAPLV--EAGTQV
HCAVI     MTVA--DG---IVYIAQQMHFHWGGASSEISGSEHTVDGIRHVIEIHIVH-YNS-KYKTYDIAQDAPDGLAVLAAFVEVNY-PE
HCAVII    RTVVTGGPLEGPYRLKQFHFHWG---KKHDVGSEHTVDGKSFPSELRLVH-WNAKKYSTFGEAASAPDGLAVVGVFL--ETG-DE
HCAV      ASGISGGPLENHYRLKQFHFHWG---AVNEGGSEHTVDGHAYPAELRLVH-MNSVKYQNYKEAVVGENGLAVIGVPL--KIG-AH
HCAVIII   --MHIQG--LQSRYSATQLHLHWG--NPNDPHGSEHTVSGQHFAABLRIVH-YNSDLYPDASTASNKSEGLAVLAVLI--EMG-SF

HCAI      NPKLQKVLDALQAIKTKGKRAPFTNFDPSTLLPSSL---DFWTYPGSLTHPPLTESVTWIICKESISVSSEQLAQF-RSLLSNV
HCAII     KPGLQKVVDVLDSIKTKGKSADFTNFDPRGLLPESL---DYWTYPGSLTTPPLLECVTWIVLKEPISVSSEQVLKF-RKINFNG
HCAIII    NGEFQIFLDALDKIKTKGKEAPFTKFDPSCLFPACR---DYWTYQGSFTPTPPCEECIVWLLLAKEPMTVSSDQMARL-RSLLSSA
HCAIV     NEGFQPLVEALSNIPKPEMSTTMAESSLLDLLPKEEKLRHYFRYLGSLLTTPTCDEKVWTVFREPIQLHREQILAFSQKL--YY
HCAVI     NTYYSNFISHLANIKYPGQRTTLTGLDVQDMLPRNLQ---HYYTTHGSLTTPPCTENVHWFVLADFVKLENSLLDHR
HCAVII    HPSMNRLVTDALYMVRFKGTKAQFSCFNPKCLLPAS---RHYMTYPGSLTTPPLSESVTWTIVLREPICISERQMGKF-RSLLFTS
HCAV      HQTLQRLVDILPEIKHDARAAMRPFDPSTLLPTCM---DYWTYAGSLTTPPLTESVTWIIQKEPVEVAPSQLSAP-RTLLFSA
HCAVIII   NPSYDKIPSHLQHVYKGQEAFVPGFNIEELLPERT---AEYRYRGSLTTPPCNFVLMTVFRNPVQISEQLLALETALYCTH

HCAI      EGDNAVPMQHNN--RPTQPLKGRTVRASF
HCAII     EGEPEELMVDNW--RPAQPLKNRQIKASFK
HCAIII    ENEPPVPLVSNM--RPPQPINNRVVRASFK
HCAIV     DKEQTVSMKDNV--RPLQQLGQRTVIKSGAPGRPLPMALPALLGPMLACLLAGFLR
HCAVI     NKTIH------MDYRRTQPLKHRVVE-SNFPNQBYTLGSEFQFYLHKIEEILDYLRRALN
HCAVII    EDDERI--HMVNNFRPPQPLKGRVVKASFRA
HCAV      LGEEK--MHVMNYRPLQPLMNRKVWASFQATNEGTRS
HCAVIII   MDDPSPREMIMWFRQVQRFDERLVTBFSQVQVCTAAGLSLGIILSLALAGILGICIVVVSIWLFRKSIKKGDNKGVIYKPA

HCAVIII   TKMETEAHA*
```

LUNG CANCER MARKER

This application is a divisional of U.S. Ser. No. 08/276,919, filed 19 Jul. 1994, now U.S. Pat. No. 5,589,579 and a 371 of PCT/ US95/09145, filed 19 Jul. 1995.

TECHNICAL FIELD

The invention relates to genes and proteins specific for certain cancers and methods for their detection.

BACKGROUND OF THE INVENTION

Lung cancer is the most common form of cancer in the world. Estimates for the year 1985 indicate that there were about 900,000 cases of lung cancer worldwide. (Parkin, et al., "Estimates of the worldwide incidence of eighteen major cancers in 1985," *Int J Cancer* 1993; 54:594–606). For the United States alone, 1993 projections placed the number of new lung cancer cases at 170,000, with a mortality of about 88%. (Boring, et al., "Cancer statistics," *CA Cancer J Clin* 1993; 43:7–26). Although the occurrence of breast cancer is slightly more common in the United States, lung cancer is second behind prostate cancer for males and third behind breast and colorectal cancers for women. Yet, lung cancer is the most common cause of cancer deaths.

The World Health Organization classifies lung cancer into four major histological types: (1) squamous cell carcinoma (SCC), (2) adenocarcinoma, (3) large cell carcinoma, and (4) small cell lung carcinoma (SCLC). (The World Health Organization, "The World Health Organization histological typing of lung tumours," *Am J Clin Pathol* 1982; 77:123–136). However, there is a great deal of tumor heterogeneity even within the various subtypes, and it is not uncommon for lung cancer to have features of more than one morphologic subtype. The term non-small cell lung carcinoma (NSCLC) includes squamous, adenocarcinoma and large cell carcinomas.

Typically, a combination of X-ray and sputum cytology is used to diagnose lung cancer. Unfortunately, by the time a patient seeks medical help for their symptoms, the cancer is at such an advanced state it is usually incurable. *Cancer Facts and Figures (based on rates from NCI SEER Program 1977–1981)*, New York: American Cancer Society, 1986). Routine large-scale radiologic or cytologic screening of smokers has been investigated. Studies concluded that cyto-morphological screening did not significantly reduce the mortality rate from lung cancer and was not recommended for routine use. ("Early lung cancer detection: summary & conclusions," *Am Rev Respir Dis* 1984; 130:565–70). However, in a subpopulation of patients where the cancer is diagnosed at a very early stage and the lung is surgically resectioned, there is a 5-year survival rate of 70–90%. (Flehinger, et al., "The effect of surgical treatment on survival from early lung cancer," *Chest;* 1992, 101:1013–1018; Melamed, et al., "Screening for early lung cancer: results of the Memorial Sloan-Kettering Study in New York," *Chest;* 1984 86:44–53). Therefore, research has focused on early detection of tumor markers before the cancer becomes clinically apparent and while the cancer is still localized and amenable to therapy.

The identification of antigens associated with lung cancer has stimulated considerable interest because of their use in screening, diagnosis, clinical management, and potential treatment of lung cancer. International workshops have attempted to classify the lung cancer antigens into 15 possible clusters that may define histologic origins. (Souhami, et al., "Antigens of lung cancer: results of the second international workshop on lung cancer antigens," *JNCI* 1991; 83:609–612). As of 1988, more than 200 monoclonal antibodies (MAb) have been reported to react with human lung tumors. (Radosevich, et al., "Monoclonal antibody assays for lung cancer," In: *Cancer Diagnosis in Vitro Using Monoclonal Antibodies*. Edited by H. A. Kupchik. New York: Marcel Dekker, 1988).

MAbs for lung cancer were first developed to distinguish NSCLC from SCLC. (Mulshine, et al., "Monoclonal antibodies that distinguish nonsmall-cell from small-cell lung cancer," *J Immunol* 1983; 121:497–502). In most cases, the identity of the cell surface antigen with which a particular antibody reacts is not known, or has not been well characterized. (Scott, et al., "Early lung cancer detection using monoclonal antibodies," In: *Lung Cancer*. Edited by J. A. Roth, J. D. Cox, and W. K. Hong. Boston: Blackwell Scientific Publications, 1993).

MAbs have been used in the immunocytochemical staining of sputum samples to predict the progression of lung cancer. (Tockman, et al., "Sensitive and specific monoclonal antibody recognition of human lung cancer antigen on preserved sputum cells: a new approach to early lung cancer detection," *J Clin Oncol* 1988; 6:1685–1693). In the study, two MAbs were utilized, 624H12 which binds a glycolipid antigen expressed in SCLC and 703D4 which is directed to a protein antigen of NSCLC. Of the sputum specimens from participants who progressed to lung cancer, two-thirds showed positive reactivity with either the SCLC or the NSCLC MAb. In contrast, of those that did not progress to lung cancer, 35 of 40 did not react with the SCLC or NSCLC Mab. This study suggests the need for the development of additional early detection targets to discover the onset of malignancy at the earliest possible stage.

Carcinoembryonic antigen (CEA) is a frequently studied tumor marker of cancer including lung cancer. (Nutini, et al., "Serum NSE, CEA, CT, CA 15-3 levels in human lung cancer," *Int J Biol Markers* 1990; 5:198–202). Squamous cell carcinoma antigen is another established serum marker. (Margolis, et al., "Serum tumor markers in non-small cell lung cancer," *Cancer* 1994; 73:605–609.). Other serum antigens for lung cancer include antigens recognized by MAbs 5E8, 5C7, and 1F10, the combination of which distinguishes between patients with lung cancer from those without. (Schepart, et al., "Monoclonal antibody-mediated detection of lung cancer antigens in serum," *Am Rev Respir Dis* 1988; 138:1434–8) Furthermore, the combination of 5E8, 5C7 and 1F10 was more sensitive, specific and accurate for identifying NSCLC when compared to results from a combination of the CEA and squamous cell carcinoma antigen tests. (Margolis, et al., Cancer 1994; 73:605–609).

Serum CA 125, initially described as an ovarian cancer-associated antigen, has been investigated for its use as a prognostic factor in NSCLC. (Diez, et al., "Prognostic significance of serum CA 125 antigen assay in patients with non-small cell lung cancer," *Cancer* 1994; 73:136876). The study determined that the preoperative serum level of CA 125 antigen is inversely correlated with survival and tumor relapse in NSCLC.

Despite the numerous examples of MAb applications, none has yet emerged that has changed clinical practice. (Mulshine, et al., "Applications of monoclonal antibodies in the treatment of solid tumors," In: *Biologic Therapy of Cancer*. Edited by V. T. Devita, S. Hellman, and S. A. Rosenberg. Philadelphia: JB Lippincott, 1991, pp. 563–588). MAbs alone may not be the answer to early detection because there has only been moderate success with immunologic reagents for paraffin-embedded tissue. Secondly, lung cancer may express features that cannot be differentiated by antibodies; for example, chromosomal deletions, gene amplification, or translocation and alteration in enzymatic activity.

After the gene to the MAb recognized surface antigen has been cloned, cytogenetic and molecular techniques may provide powerful tools for screening, diagnosis, management and ultimately treatment of lung cancer. An example of a lung cancer antigen that has been cloned is the adenocarcinoma-associated antigen. This antigen, recognized by KS1/4 MAb, is an epithelial malignancy/epithelial tissue glycoprotein from the human lung adenocarcinoma cell line UCLA-P3. (Strand, et al., "Molecular cloning and characterization of a human adenocarcinoma/epithelial cell surface antigen complementary DNA," *Cancer Res* 1989; 49:314–317). The antigen has been found on all adenocarcinoma cells tested and in various corresponding normal epithelial cells. Northern blot analysis indicated that transcription of the adenocarcinoma-associated antigen was detected in RNA isolated from normal colon but not in RNA isolated from normal lung, prostate, or liver. Therefore identification of adenocarcinoma-associated antigen in lung cells may prove to be diagnostic for adenocarcinoma.

The cloning of CEA and the nonspecific crossreacting antigen (NCA) has allowed the development of specific DNA probes which discriminate their expression in lung cancer at the mRNA level. (Hasegawa, et al., "Nonspecific crossreacting antigen (NCA) is a major member of the CEA-related gene family expressed in lung cancer," *Br J Cancer* 1993; 67:58–65). NCA is a component of the CEA gene family in lung cancer and is also recognized by anti-CEA antibodies, especially polyclonal antibodies. Because of the crossreactivity, investigations to analyze CEA and NCA separately in lung disease had been difficult. The use of DNA probes determined that lung cancer cells fall into three different types according to their CEA and/or NCA expression by Northern blot analysis. Specifically, lung cancers expressed both CEA and NCA mRNA, only NCA mRNA, or neither mRNA. CEA-related mRNA expression was always accompanied by NCA mRNA expression and there were no cases of CEA mRNA expression alone. The separate assessment of CEA and NCA expression in lung cancers may be important in determining the prognosis of lung cancers because the antigens have been described as cell-cell adhesion molecules and may play a role in cancer metastasis.

Another method to detect the presence of an antigen gene or its mRNA in specific cells or to localize an antigen gene to a specific locus on a chromosome is in situ hybridization. In situ hybridization uses nucleic acid probes that recognize either repetitive sequences on a chromosome or sequences along the whole chromosome length or chromosome segments. By tagging the probes with radioisotopes or color detection systems, chromosome regions can be identified within the cell. Investigations using in situ hybridization have demonstrated numerical chromosomal abnormalities in samples from human tumors, including bladder, neuroectodermal, breast, gastric and lung cancer tumors. (Kim, et al., "Interphase cytogenetics in paraffin sections of lung tumors by non-isotopic in situ hybridization. Mapping Genotype/phenotype heterogeneity," *Am J Pathol* 1993; 142:307–317).

Fluorescence in situ hybridization (FISH) allows cells to be stained so that genetic aberrations resulting in changes in gene copy number or structure can be quantitated by fluorescence microscopy. In this technique, a chemically labeled single-stranded nucleic acid probe homologous to the target nucleic acid sequence is annealed to denatured nucleic acid contained in target cells. The cells may be mounted on a microscope slide, in suspension or prepared from paraffin-embedded material. Treating the chemically modified probes with a fluorescent ligand makes the bound probe visible. FISH has been used for (1) detection of changes in gene copy number and gene structure; (2) detection of genetic changes, even in low frequency subpopulations; and (3) detection and measurement of the frequency of residual malignant cells. (Gray, et al., "Molecular cytogenetics in human cancer diagnosis," *Cancer* 1992; 69:1536–1542).

Other molecular markers for lung cancer include oncogenes and tumor suppressor genes. Dominant oncogenes are activated by mutation and lead to deregulated cellular growth. Such genes code for proteins that function as growth factors, growth factor receptors, signal transducing proteins and nuclear proteins involved in transcriptional regulation. Amplification, mutation, and translocations have been documented in many different cancer cells and have been shown to lead to gene activation or overexpression.

The ras family of oncogenes comprises a group of membrane associated GTP-binding proteins thought to be involved in signal transduction. Mutations within the ras oncogenes, resulting in sustained growth stimulation, have been identified in 15 to 30% of human NSCLC. (Birrer, et al., "Application of molecular genetics to the early diagnosis and screening of lung cancer," Cancer 1992; 52suppl; 2658s–2664s). Patients with tumors containing ras mutations had decreased survival compared with patients whose tumors had no ras mutations. Polymerase chain reaction (PCR) amplification of ras genes can be analyzed to determine the presence of mutations by several methods: (a) differential hybridization of $^{32}$P-labeled mutated oligonucleotides; (b) identification of new restriction enzyme sites created by the activating mutation; (c) single-strand conformational polymorphisms; and (d) nucleic acid sequencing. These methods combined with PCR technology could allow detection of an activated ras gene from sputum specimens.

Another family of dominant oncogenes, the erb B family, has been found to be abnormally expressed in lung cancer cells. This group codes for membrane-associated tyrosine kinase proteins and contains erb B1, the gene coding for the epidermal growth factor (EGF) receptor, and erb B2 (also called Her-2/neu). The erb B1 gene has been found to be amplified in NSCLC (up to 20% of squamous cell tumors), while the EGF receptor has been shown to be overexpressed in many NSCLC cells (approximately 90% of squamous cell tumors, 20 to 75% of adenocarcinomas, and rarely in large cell or undifferentiated tumors). (Birrer, et al., *Cancer* 1992: 52 suppl; 2658s–2664s). Amplification of the related oncogene erb B2 (Her-2/neu) occurs infrequently in lung cancer but is a negative prognostic factor in breast cancer. However, overexpression of the erb B2 protein product, p185$^{neu}$, occurs in some NSCLC and may be related to poor prognosis. (Kern, et al., "p185$^{neu}$ expression in human lung adenocarcinomas predicts shortened survival," *Cancer Res* 1990; 50:5184–5191).

A third family of dominant oncogenes involved in lung cancer is the myc family. These genes encode nuclear phosphoproteins, which have potent effects on cell growth and which function as transcriptional regulators. Unlike ras genes, which are activated by point mutations in lung cancer cells, the myc genes are activated by overexpression of the cellular myc genes, either by gene amplification or by rearrangements, each ultimately leading to increased levels of myc protein. Amplification of the normal myc genes is seen frequently in SCLC and rarely in NSCLC.

The loss or inactivation of tumor suppressor genes may also be important steps in the pathway leading to invasive cancer. Tumor suppressor genes function normally to suppress cellular proliferation, and since they are recessive oncogenes, mutations or deletions must occur in both alleles of these genes before transformation occurs.

A phosphoprotein p53, which is encoded by a gene located on chromosome 17p, suppresses transformation in its wild-type state. While in its mutant state, p53 acts as a dominant oncogene. p53 functions in DNA binding and transcription activation. Mutations of p53 have been found in many human cancers including colon, breast, brain and lung cancer cells. (Birrer, et al., *Cancer Res.* (suppl) 1992, 52:2658s–2664s). In NSCLC cell lines, p53 mutations have been found at a rate of up to 74%. (Mitsudomi, et al., "p53 gene mutations in non-small-cell lung cancer cell lines and their correlation with the presence of ras mutations and clinical features," *Oncogene* 1992; 7:171–180).

Despite all of the advances made in the area of lung cancer, medical and surgical intervention has resulted in little change in the 5-year survival rate for lung cancer patients. Early detection holds the greatest hope for successful intervention. There remains a need for a practical method to diagnose lung cancer as close to its inception as possible. In order for early detection to be feasible, it is important that specific markers be found and their sequences elucidated.

A lung cancer marker antigen, specific for NSCLC, has now been found, sequenced, and cloned. The antigen is useful in methods for detection of non-small cell lung cancer and for potential production of antibodies and probes for treatment compositions.

SUMMARY OF THE INVENTION

The invention concerns a lung cancer antigen (HCAVIII) gene specific for non-small cell lung cancer.

In one embodiment, the invention relates to a substantially purified nucleic acid (SEQ ID NO:1) encoding the pre-protein sequence shown in SEQ ID NO:2.

In other embodiments, the invention relates to cDNAs which encode the mature form of the protein (SEQ ID NO:4), or a truncated form of the protein lacking the transmembrane domain (SEQ ID NO:13 and SEQ ID NO:15), or a protein in which one or more of the amino acids in the phosphorylation region have been altered to affect that function, an example of which is shown in SEQ ID NO:18.

In other embodiments, proteins encoded by the cDNA of SEQ ID NO:1, SEQ ID NO:3, SEQ ID NO:5, SEQ ID NO:12, SEQ ID NO:14, and SEQ ID NO:17 are provided.

In another aspect, the invention relates to a recombinant DNA clone for HCAVIII.

In further aspects of the invention, expression vectors for HCAVIII and modifications thereof are an object.

The invention further relates to methods of detecting lung cancer.

In one aspect an in situ hybridization technique is provided. In another aspect, a fluorescence in situ hybridization technique is provided. In a further aspect, an ELISA assay is provided. In another aspect, detection of carbonic anhydrase activity which correlates with lung cancer antigen is provided.

BRIEF DESCRIPTION OF THE DRAWING

FIG. 1 depicts the alignment of the amino acid sequence of HCAVIII with previously described carbonic anhydrases. Conserved amino acids are shown in bold.

DETAILED DESCRIPTION OF THE INVENTION

The nucleic acid sequence coding for a cell surface protein (said protein hereinafter designated HCAVIII) which is highly specific for non-small cell lung cancer cells has now been obtained. This gene sequence will facilitate detection and treatment of the disease, which to date has often proven difficult.

The HCAVIII cDNA in the vector pLC56 has been sequenced and characterized including the entire coding region and substantially all of the upstream and downstream non-translated regions. The cDNA in pLC56 was sequenced on both strands from exonuclease III-generated deletions and subsequent subcloning into M13 vectors or directly from the cloning vectors using the di-deoxy method and a SEQUENASE ® Version 2.0 kit (U.S. Biochemicals, Cleveland, Ohio). Additional regions of DNA were subcloned as small restriction fragments into the same vectors for sequence analysis. Overlapping segments were ordered using MacVector Align software (Kodak/IBI Technologies, New Haven Conn.). SEQ ID NO:1 represents the cDNA encoding HCAVIII and a presumed signal peptide. SEQ ID NO:2 represents the signal peptide (amino acid residues −29 to −1) followed by the mature protein (amino acid residues 1 to 325). As predicted from the cDNA sequence in pLC56, a protein of about 354 amino acids is encoded with the predictive size of 39448 daltons. A hydrophilicity plot (MacVector software, Kodak/IBI Technologies) of this protein provided strong evidence of a leader peptide at the N-terminus and a membrane-spanning segment near the C-terminus. The membrane-spanning segment provides evidence that this protein is membrane bound, as also predicted by its positive selection with panning methodology (See Watson, et al., *Recombinant DNA*, 2nd ed., pp. 115–116, 1992). The cleavage site of the signal as predicted by von Heijne (von Heijne, Gunnar, *Nucleic Acids Res* 1986; 14:4683–4690) is 29 amino acids down from the N-terminus methionine. SEQ ID NO:3 corresponds approximately to the coding region of the mature polypeptide. The subsequent "mature" protein is proposed to be 325 amino acids, initiating with serine, and of a calculated 36401 daltons and a pI of 6.42 (SEQ ID NO:4).

Homology searches against NCBI BlastN or BlastX version 1.3.12MP (National Center for Biotechnology Information, Bethesda, Md.) provided evidence the gene and protein are novel, not previously identified in either database. (Altschul, et al., "Basic local alignment search tool," *J Mol Biol* 1990; 215:403–410). Additional searches against another database (Entrez, version 9) gave similar results.

The isolation of a second cDNA encoding HCAVIII permitted the identification of new sequences within the 5'-and 3'-prime untranslated regions of this gene. SEQ ID NO:5, a cDNA encoding HCAVIII and a portion of the 5' and 3' nontranslated regions, has substantial identity with SEQ ID NO:1 (positions 1–1104 of SEQ ID NO:1 are identical to positions 85–1188 of SEQ ID NO:5). The encoded protein is listed in SEQ ID NO:6 and is identical with SEQ ID NO:2. Homology searches of NCBI BlastN against SEQ ID NO:5 showed these gene sequences have not been previously identified. SEQ ID NO:7 represents additional cDNA sequences of the 3' nontranslated region of the HCAVIII gene located downstream from the sequences depicted in SEQ ID NO:5. Homology searches against the same data base identified two clones with homology to SEQ ID NO:7. Both sequences are expressed sequence tags (EST), the first EST04899 (345 bp) and the second HUMGS04024 (466 bp).

Alignment searches indicate this protein shares common features with the seven human carbonic anhydrase proteins previously identified. However, as described below, certain structural features distinct to HCAVIII exist that may confer unique properties to this protein and a role in the transformation pathway to tumorgenicity. This group of enzymes catalyze the hydration of carbon dioxide $$CO_2 + H_2O \leftrightharpoons HCO_3 + H^+$$

and in reverse the dehydration of $HCO_3^-$. This protein is identified as a carbonic anhydrase (CA) based on the conservation of amino acids at positions critical for the binding of $Zn^{+2}$, and the catalysis of $CO_2$, as well as numerous other conserved amino acids (see FIG. 1). The protein is 34 to 64 amino acids longer (at the C-terminus) than any previously reported carbonic anhydrase by virtue of the membrane-spanning region also found in HCAIV and an additional approximate 30 amino acids contained in the cytoplasmic side of the cell and apparently missing in other human CA isoforms. In addition, this intracellular domain contains a phosphorylation site recognized by protein kinase C and other kinases, as defined by the motif "Arg-Arg-Lys-Ser" (SEQ ID NO:8 and SEQ ID NO:9) (amino acid residues 1–4 in SEQ ID NO:9 and amino acid residues 299–302 in SEQ ID NO:2, SEQ ID NO:4 and SEQ ID NO:6).

Interestingly, this motif is found only in HCAVIII, and at a functionally significant site, i.e., within the cytosol. A surface cleft essential for enzymatic function present on other carbonic anhydrases is conserved for this protein, suggesting that this protein will also confer enzymatic activity. Five possible N-glycosylation sites are predicted by the primary amino acid sequence and the motif "Asn-Xaa-Ser (Thr)", beginning at amino acid residues −2, 51, 133, 151, and 202 in SEQ ID NO:2, respectively.

HCAVIII is expressed at a much higher level in a non-small cell lung cancer cell line (A549) than in normal lung tissue, other normal tissues, and other tumor cell lines which makes it useful in distinguishing this disease. This is clearly demonstrated in Table 1. Data for this table was obtained as follows. Total cellular RNA was isolated from the indicated actively growing cell lines as described by Chirgwin, et al., "Isolation of biologically active ribonucleic acid from sources enriched in ribonuclease," *Biochemistry* 1979; 18:5294–5299. RNA samples were fractionated over a 1% agarose-formaldehyde gel and transferred to a nylon membrane (Qiagen, Chatsworth, Calif.) by capillary action. The hybridization probe was generated from a 1 kilobase pair BstXI restriction fragment isolated from pLC56, a plasmid harboring the HCAVIII gene in its initial isolation. This fragment was radiolabeled with 32p using a PRIME-IT® Random Primer Labeling Kit obtained from Stratagene, La Jolla, Calif. A membrane containing RNA derived from healthy human tissue was purchased from Clonetech Laboratories, Inc., Palo Alto, Calif. RNA blots were hybridized in a standard cocktail containing $^{32}P$-labeled probe at 42° C. overnight then exposed to X-ray film. The same blots were subsequently, upon removal of the probe, rehybridized with a second $^{32}P$-labeled DNA from β-actin to serve as a positive control for integrity of the blotted RNA.

As shown in Table 1, normal lung tissue does not express the HCAVIII gene in detectable amounts. Other tumor cell lines fail to express, or express only in minor amounts, which will allow easy distinction of non-small cell carcinomas.

TABLE 1

NORTHERN BLOTS USING HCAVIII cDNA AGAINST NORMAL TISSUES AND TUMOR CELL LINES

| TISSUE | mRNA (kB) | INTENSITY |
|---|---|---|
| NORMAL TISSUE | | |
| heart | nd[1] | — |
| brain | 4.5 | 1×[2] |
| placenta | 4.5 | 1× |
| lung | nd | — |
| liver | nd | — |
| skeletal muscle | nd | — |
| kidney | 4.5 | 100× |
| pancreas | 4.5 | 10× |
| TUMOR CELL LINE | | |
| A549 (lung carcinoma) | 3.5 | 5000× |
|  | 5.4 | 50× |
|  | 8.0 | 25× |
|  | 9.0 | 25× |
| BT20 (breast carcinoma) | nd | — |
| G361 (melanoma) | nd | — |
| HT144 (melanoma) | nd | — |
| U937 (histiocytic lymphoma) | nd | — |
| KG-1 (myelogenous leukemia) | nd | — |

[1]nd = none detected
[2]1× = at limit of detection

In one embodiment of the invention, probes are made corresponding to sequences of the cDNA shown in SEQ ID NO:3, which are complimentary to the mRNA for HCAVIII. These probes can be radioactively or non-radioactively labeled in a number of ways well known to the art. The probes can be made of various lengths. Such factors as stringency and GC content may influence the desired probe length for particular applications. The probes correspond to a length of 10–986 nucleotides from SEQ ID NO:3. The labeled probes can then be bound to detect the presence or absence of mRNA encoding the HCAVIII in biopsy material through in situ hybridization. The MRNA is expected to be associated with the presence of non-small cell tumors and to be a marker for the precancerous condition as well.

In situ hybridization provides a specificity to the target tissue that is not obtainable in Northern, PCR or other probe-driven technologies. In situ hybridization permits localization of signal in mixed-tissue specimens commonly found in most tumors and is compatible with many histologic staining procedures. This technique is comprised of three basic components: first is the preparation of the tissue sample provided by the pathologist to permit successful hybridization to the probe. Second is the preparation of the hybridization probe, typically a RNA complementary to the mRNA of the gene of interest (i.e., antisense RNA). RNA probes are preferred over DNA probes for in situ hybridizations mainly because background hybridization of the probe to irrelevant nucleic acids or nonspecific attachment to cell debris or subcellular organelles can be eliminated with RNAse treatment post-hybridization. Third is the hybridization and post-hybridization detection. Typically the RNA transcript probe has been radiolabeled by the incorporation of $^{32}P$ or $^{35}S$ nucleotides to permit subsequent detection of the probed specimen by autoradiography or quantitation of silver grains following treatment with autoradiographic emulsion. Nonradioactive detection systems have also been developed. In one example, biotinylated nucleotides can be substituted for the radioactive nucleotide in the RNA probe preparation, permitting visualization of the probed sample by immunocytochemistry-derived techniques. Example 1 describes in situ hybridization procedures using RNA probes derived from the HCAVIII gene. Example 2 provides exemplary fluorescent in situ (FISH) hybridization procedures.

The cDNA for HCAVIII (SEQ ID NO:3) is currently in an expression vector which is be used to generate the protein in *E. coli*. This expression system described in Example 3 produces HCAVIII to be used as an antigen for the generation of antibodies (Example 4) for use in an ELISA assay to detect shed HCAVIII in body fluids as described in Example 5. The methods for production of antibodies and ELISA type assays are well known in the art. Exemplary methods and components of these procedures have been chosen and developed and are described in Examples 4 and 5.

The expression and purification of foreign proteins in *E. coli* is often problematic. On occasion, the protein is expressed at high levels but is deposited within the cell as an insoluble, denatured form termed an inclusion body. These bodies are often observed when the foreign protein contains a hydrophobic domain, such as found in the membrane spanning segment of HCAVIII. Through recombinant DNA technology, the DNA sequences encoding the membrane spanning segment of HCAVIII are deleted. The protein expressed in *E. coli* from this engineered plasmid is now in a soluble and native form within the cell, permitting a rapid and less harsh purification. In addition, the ELISA test to measure HCAVIII shed into body fluids as described in Example 5 relies on the recombinant protein produced from *E. coli*. Typically, the shed antigen is a membrane-bound receptor that was released from the membrane spanning segment anchoring it to the cell. Consequently, the recombinant HCAVIII engineered to remove the membrane spanning segment is a more accurate representation of the putative HCAVIII shed antigen found in specimens and may prove to be the preferred antigen for polyclonal antisera and monoclonal antibody production as described for the development of an ELISA test.

To produce the engineered plasmid, a first plasmid is constructed by cleaving pLC56 with the restriction enzyme Tth111 I, followed by treatment with $T_4$-DNA polymerase and dGTP, DATP, dTTP and dCTP, and finally with alkaline phosphatase to remove 5'-terminal phosphates. The DNA sample is then purified by phenol/chloroform extraction and ethanol precipitation. The sample is digested with the restriction endonuclease BspE1, then the fragments are resolved by agarose gel electrophoresis to permit the isolation of a 267 base pair fragment. A second plasmid described previously for expression of the HCAVIII mature protein (SEQ ID NO:4), is cleaved with EcoRI and BspE1 followed by alkaline phosphatase treatment and purification by phenol/chloroform extraction and ethanol precipitation. Two oligonucleotides are synthesized, being 5'-TGAGTCGACG (SEQ ID NO:10) and 5'-AATTCGTCGACTCA (SEQ ID NO:11), that complement each other and upon annealing, provide a termination codon (TGA) and sequence complementary to EcoRI cleaved DNA. Finally, the two oligonucleotides, the 267 base pair fragment, and the BspEI/EcoRI cleaved plasmid will be combined in a ligation reaction, and the resultant plasmid which contains the truncated DNA sequence (SEQ ID NO:12) is used to transform competent *E. coli*. Upon expression in *E. coli*, the resulting truncated protein (SEQ ID NO:13) is 271 amino acids as determined by SDS polyacrylamide electrophoresis and of a size consistent with other HCA's but lacking the membrane spanning segment and the intracellular domain. A second plasmid encoding a HCAVIII truncated protein (SEQ ID NO:14) lacking the membrane spanning segment and intracellular domain was created as described above, except that restriction enzyme Ple I was substituted for Tth111 I, resulting in a gel purified DNA fragment of 276 base pairs. Upon expression in *E. coli*, the resulting protein is now 274 amino acids (SEQ ID NO:15).

An understanding of protein phosphorylation and its role in the mechanism of cell transformation has been actively pursued, most notably with tyrosine phosphorylation and oncogene activation. The role of serine/threonine protein phosphorylation by a variety of protein kinases including protein kinase C has been studied extensively with respect to signal transduction, but its role in oncogenesis is less clear. To provide a valuable tool to be used in the study of the role of HCAVIII serine phosphorylation in oncogenesis, an altered cDNA can be prepared to code for an altered protein. Changes to amino acids other than "Gly" may be realized by alterations to the oligonucleotide sequence (SEQ ID NO:16) used to encode the selected residue. Other modifications to alter the serine phosphorylation site would utilize the described technology to modify either both "Arg" residues located within SEQ ID NO:9 or amino acid residues 299 and 300 of SEQ ID NO:2, SEQ ID NO:4 and SEQ ID NO:6. Since "Arg" residues contain a net positive charge, the substituted amino acids would preferably be "Lys" or "His," also positively charged amino acids. An exemplary plasmid is produced in which the "Ser" codon (amino acid residue 4 of SEQ ID NO:9; amino acid residue 302 in SEQ ID NO:2, SEQ ID NO:4 and SEQ ID NO:6), is converted to a "Gly" codon using an in vitro mutagenesis technique described in Example 3 and previously recited in Kunkel, Thomas, "Rapid and efficient site-specific mutagenesis without phenotypic selection," *Proc Natl Acad Sci USA* 1985; 82:488–492, and the oligonucleotide 5'-CTTTTTTGATACCCTTCCTTCTGAA (SEQ ID NO:16) (located in SEQ ID NO:1 at the base pairs 1010–1034 with 1022 as the mutagenized base pair). The DNA sequences containing the HCAVIII gene engineered for production of the mature protein and mutagenized codon is released from the mutagenesis vector by BamHI and EcoRI restriction endonucleases and ligated into pGEX4T1 cleaved with the same enzymes, and the resultant plasmid is used to transform competent *E. coli*. The codon mutagenesis is confirmed by DNA sequence analysis, and the protein is expressed and purified from *E. coli* as described in Example 3. The DNA sequence of the altered plasmid as shown in SEQ ID NO:17 differs from the gene encoding the mature protein (SEQ ID NO:3) in that the nucleotide 1022 is changed from "A" to "G", and the protein sequence (SEQ ID NO:18) expressed by the altered plasmid is identical to the mature protein (SEQ ID NO:4) except that amino acid residue 302 is changed from "Ser" to "Gly."

Another way to detect the presence of increased HCAVIII could be to assay for levels of carbonic anhydrase activity in biopsy materials as described in Example 6. This should be a useful test as HCAVIII, although it is an immunologically unique molecule, contains small but distinct regions which are conserved between previously reported carbonic anhydrase proteins.

In another embodiment of the invention, primers are made complimentary to the HCAVIII cDNA (SEQ ID NO:3) for detecting expression of the gene. PCR amplification of cDNA from lung biopsy cells would indicate the presence of the same non-small cell lung carcinoma.

Due to the non-small cell lung cancer specificity of HCAVIII and the gene encoding the protein, antibodies specific for HCAVIII would also exhibit non-small cell lung cancer specificity which can be employed for diagnostic detection of HCAVIII in body fluids such as serum or urine or HCAVIII containing cells. Targeting of cancer therapeutic drugs to HCAVIII containing cells can also be developed using HCAVIII specific antibodies. The genetic expression of the gene encoding HCAVIII could be modulated by drugs or anti-sense technology resulting in an alteration of the cancer state of the HCAVIII containing cells.

EXAMPLE 1

In Situ Hybridization using RNA Probes Derived from the HCAVIII Gene

Tissue samples are treated with 4% paraformaldehyde (or equivalent fixative), dehydrated in sequential ethanol solutions of increasing concentrations (e.g., 70%, 95% and 100%) with a final xylene incubation (see Current Protocols in Molecular Biology, pp. 14.01–14.3 and Immunocytochemistry II:IBRO Handbook Series: Methods in the Neurosciences Vol 14; pp 281–300, incorporated herein by reference). The tissue is embedded in molten paraffin, molded in a casting block and can be stored at room temperature. Tissue slices, typically 8 μm thick, are prepared with a microtome, dried onto gelatin-treated glass slides and stored at −20° C.

DNA sequences from the HCAVIII gene (SEQ ID NO:3) are subcloned into a plasmid engineered for production of RNA probes. In this example, a 776 bp DNA fragment is released from a pLC56 plasmid following BamHI/AccI digestion, where the BamHI site has been created by in vitro mutagenesis (see E. coli expression below). This fragment is ligated into pGEM-2 (Promega Biotec, Madison, Wis.) that was cleaved with BamHI and AccI and transformed into competent E. coli. This constructed plasmid contains the T7 RNA polymerase promoter downstream of the AccI restriction site and hence can drive transcription of the antisense HCAVIII sequences defined by the BamHI/AccI fragment. Following linearization of the subsequent plasmid with BamHI, an in vitro transcription reaction composed of transcription buffer (40 mM Tris-HCl, pH 7.5, 6 mM MgCl$_2$, 2 mM spermidine, 10 mM NaCl, 10 mM dithiothreitol, 1 U/ul ribonuclease inhibitor), linearized plasmid, 10 mM GTP, 10 mM ATP, 10 mM CTP, 100 μCi of ($^{35}$S)UTP, and T7 RNA polymerase is incubated at 37° C. Multiple RNA copies of the gene are produced that then are used as a hybridization probe. The reaction is terminated by the addition of DNAase, and the synthesized RNA is recovered from unincorporated nucleotides by phenol/chloroform extraction and sequential ethanol precipitations in the presence of 2.5M ammonium acetate.

The slides containing fixed, sectioned tissues are rehydrated in decreasing concentration of ethanol (100%, 70% and 50%), followed by sequential treatments with 0.2N HCl, 2× SSC (where 20× SSC is 3M NaCl and 0.3M sodium citrate) at 70° C. to deparaffinate the sample, phosphate buffered saline (PBS), fixation in 4% paraformaldehyde and PBS wash. The slides are blocked to prevent nonspecific binding by the sequential additions of PBS/10 mM dithiothreitol (45° C.), 10 mM dithiothreitol/0.19% iodoacetamide/0.12% N-ethylmaleimide and PBS wash. The slides are equilibrated in 0.1M triethylamine, pH 8.0, followed by treatment in 0.1M triethylamine/0.25% acetic anhydride and 0.1M triethylamine/0.5% acetic anhydride and washed in 2× SSC. The slides are then dehydrated in increasing concentrations of ethanol (50%, 70% and 100%) and stored at −80° C.

A hybridization mix is prepared by combining 50% deionized formamide, 0.3M NaCl, 10 mM Tris-HCl, pH 8.0, 1 mM EDTA, 1× Denhardt's solution (0.02% Ficoll 400, 0.02% polyvinylpyrrolidone, 0.02% bovine serum albumin (BSA)), 500 μg/ml yeast tRNA, 500 μg/ml poly(A), 50 mM dithiothreitol, 10% polyethyleneglycol 6000 and the $^{35}$S-labeled RNA probe. This solution is placed on the fixed, blocked tissue slides which are then incubated at 45° C. in a moist chamber for 0.5 to 3 hours. The slides are washed to remove unbound probe in 50% formamide, 2× SSC, 20 mM 2-mercaptoethanol (55° C.), followed by 50% formamide, 2× SSC, 20 mM 2-mercaptoethanol and 0.5% Triton-X 100 (50° C.) and finally in 2× SSC/20 mM 2-mercaptoethanol (room temperature). The slides are treated with 10 mM Tris-HCl, pH 8.0/0.3M NaCl/40 μg/ml RNase A/2 μg/ml RNAse T1 (37° C.) to reduce levels of unbound RNA probe. Following RNAse treatment, the slides are washed in formamide/SSC buffers at 50° C., room temperature and then dehydrated in increasing ethanol concentrations containing 0.3M ammonium acetate, and one final 100% ethanol wash. The slides are then exposed to X-ray film followed by emulsion autoradiography to detect silver grains.

Test tissue samples are compared to matched controls derived from normal lung tissue. Evidence of elevated transcription of the HCAVIII gene in test tissue compared to normal tissue, as determined by autoradiography (X-ray film) or alternatively by the quantitation of silver grains following emulsion autoradiography would provide evidence of a positive diagnosis for lung cancer.

EXAMPLE 2

Fluorescent In Situ Hybridization (FISH) Using DNA Probes Derived from the HCAVIII Gene A genomic clone to the HCAVIII gene (SEQ ID NO:1) is isolated using a PCR primer pair which have been identified from the pLC56 cDNA sequence. This primer pair is located in putative exon 6 of the pLC56 gene, and they are identified as Probe Exon 6A (5'-ACATTGAAGAGCTGCTTCCGG-3'; SEQ ID NO:19) and Probe Exon 6B (5'-AATTTGCACGGGGTTTCGG-3'; SEQ ID NO:20). The genomic clone of HCAVIII is then identified as a PCR product of about 119 bp using this primer pair from the designated genomic clone. This result is confirmed by Southern blotting and DNA sequence analysis. A sequence of 1363 bp derived from the HCAVIII genomic clone is reported in SEQ ID NO:21. This sequence is located directly before the HCAVIII cDNA and constitutes the putative promoter of this gene and likely contains transcription regulatory elements directly implicated in HCAVIII expression.

The DNA probe comprising the genomic clone of HCAVIII plus flanking sequences is labeled in a random primer reaction with digoxigenin-11-dUTP (Boehringer Mannheim Biochemicals, Indianapolis, Ind.) by combining the DNA with dNTP(-TTP, final 0.05 mM), digoxigenin-11-dUTP/dTTP (0.0125 mM and 0.0375 mM, final), 10 mM 2-mercaptoethanol, 50 mM Tris-HCl, pH 7.5, 10 MM MgCl$_2$, 20 U of DNA polymerase I and 1 ng/ml DNAase. The reaction is incubated at 15° C. for two hours, and then terminated by adding EDTA to a final concentration of 10 mM. The labeled DNA probe is further purified by gel filtration chromatography. It is apparent to those skilled in the art that other suitable substrates such as biotin-11-dUTP can be substituted for digoxigenin-11-dUTP in the procedure above.

A hybridization mix is prepared by combining 50% deionized formamide, 0.3 M NaCl, 10 mM Tris-HCl, pH 8.0, 1 mM EDTA, 1× Denhardt's solution (0.02% Ficoll 400, 0.02% polyvinylpyrrolidone, and 0.02% bovine serum albumin), 500 μg/ml yeast tRNA, 500 μg/ml poly(A), 50 mM dithiothreitol, 10% polyethyleneglycol 6000, and the labeled DNA probe.

Single cell suspensions of tissue biopsy material or normal tissue are fixed in methanol/glacial acetic acid (3:1 vol/vol) and dropped onto microscope slides. (Aanastasi, et al., "Detection of Trisomy 12 in chronic lymphocytic leukemia by fluorescence in situ hybridization to interphase cells: a simple and sensitive method," Blood 1992; 77:2456–2462). After the slides are heated for 1–2 hours at 60° C., the hybridization mix is applied to the slides which are then incubated at 45° C. in a moist chamber for 0.5–3 hours. After incubation, the slides are washed three times with a solution comprising 50% formamide and 2× SSC at 42° C., washed twice in 2× SSC at 42° C., and finally washed in 4× SSC at room temperature. The slide is blocked with a solution of 4× SSC and 1% BSA, and then washed with a solution of 4× SSC and 1% Triton X-100.

The hybridized digoxigenin-labeled probe is detected by adding a mixture of sheep anti-digoxigenin antibody (Boehringer Mannheim) diluted in 0.1M sodium phosphate, pH 8.0, 5% nonfat dry milk, and 0.02% sodium azide, followed by the addition of fluorescein-conjugated rabbit anti-sheep IG for detection. The slides are then washed in PBS, mounted in Vectashield (Vector Laboratories, Inc., Burlingame, Calif.), and viewed by fluorescent microscopy.

Hybridization signals are enumerated in tumor derived tissue and then compared to normal tissue. Normal tissue displays two distinct hybridization signal characteristics of a diploid state. Enumeration over the rate of two hybridization signals/cell is considered significant.

EXAMPLE 3

Expression of HCAVIII

Expression of foreign proteins is often performed in *E. coli* when an immunogen or large amounts of protein are desired, as in the development of a diagnostic kit. A preferred system for *E. coli* expression has been described (Smith, et al., "Single-step purification of polypeptides expressed in *Escherichia coli* as fusions with glutathione-s-transferase," Gene 1988; 67:31–40) whereby glutathione transferase is expressed with amino acids representing the cloned protein of interest attached to the carboxyl-terminus. The fusion protein can then be purified via affinity chromatography and the protein of interest fused to glutathione transferase released by digestion with the protease thrombin or alternatively the fusion protein is released intact from the affinity column by competing levels of free glutathione.

To express the HCAVIII protein (SEQ ID NO:4) of this invention in *E. coli* using the above described technology, an expression plasmid was produced fused to the glutathione transferase gene in frame with the HCAVIII gene (SEQ ID NO:1) to produce a fusion protein. The is fusion gene/expression plasmid was assembled from nucleic acids derived from the following sources. First, the expression plasmid pGEX4T1 (Pharmacia, Piscataway, N.J.) was cleaved in the polycloning region with the restriction endonucleases BamHI and EcoRI to permit insertion of the HCAVIII gene. Second, an oligonucleotide was synthesized, being 5'-GTCCACTTGGATCCGTTCACTGG-3' (SEQ ID NO:22). Using the in vitro mutagenesis procedure described by Kunkel (Proc Natl Acad Sci USA 1985; 82:488–492) and the above oligonucleotide, a BamHI restriction site was created without altering the amino acid codons of the original protein. In addition the created BamHI site was situated in correct reading frame and proximity to the predicted cleavage site separating the signal peptide from the mature protein. The DNA sequences encoding the mature protein were released from the mutagenesis vector as a BamHI/EcoRI fragment, where the EcoRI site originates from a polycloning region of the DNA sequencing vector pUC19 found downstream of the HCAVIII gene. The DNA fragments described above comprised of pGEX4T-1 cleaved at BamHI and EcoRI and the HCAVIII gene released as a BamHI/EcoRI fragment was combined in a mixture composed of 1× $T_4$ ligase buffer (50 mM Tris-HCl, 10 mM $MgCl_2$, 20 mM dithiothreitol, 1 mM ATP, 50 μg/ml BSA, final pH 7.5) and $T_4$ DNA ligase (New England Biolabs, Beverly, Mass.). The ligated DNA was used to transform a suitable strain of *E. coli* such as XL-1 Blue (Stratagene). The recovered plasmid is sequenced to confirm the expected DNA sequence. Protein expression is induced in *E. Coli* with the chemical isopropyl β-thiogalactoside, and the fusion protein is released by cell lysis, followed by denaturation and resolubilization of the fusion protein with 8M urea/ 20 mM Tris.Cl (pH 8.5)/10 mM dithiothreitol, dialysis and protein renaturation, and finally binding to an affinity column composed of glutathione-agarose (Sigma, St. Louis, Mo.) and cleavage with thrombin to release the HCAVIII protein. The resulting protein is suitable as an immunogen for polyclonal or monoclonal antibody production and for usage in an ELISA kit as a internal standard and positive control. Carbonic anhydrase enzyme activity (as described in Example 6) was measured for E.coli-derived HCAVIII and HCAVIII-truncated form (SEQ ID NO:15) and compared to commercially obtained human carbonic anhydrase II (Sigma, St. Louis, Mo.). The activity, as reported in Enzyme Unit (U)/mg, for human carbonic anhydrase II was 3571 U/mg, for HCAVIII was 274 U/mg and HCAVIII truncated form was 2632 U/mg. These results indicated an enzymatically active and renaturable HCAVIII derived from *E.coli* of comparable enzymatic activity to human carbonic anhydrase II was obtained.

The length of the resulting protein can be varied by altering the length of SEQ ID NO:1 prior to insertion into the expression plasmid, or by cleavage of amino acids from the protein resulting in the above example. Structure/function studies of other HCA's suggest modifications (as defined by deletions at the N-terminal and C-terminal) more extensive than disclosed in SEQ ID NO:12 would still permit the production and use of a protein as an immunogen or standard, these deletions being a protein defined by about amino acid residue 3 to amino acid residue 259 in SEQ ID NO:12. Using existing technology one could synthesize a peptide of approximately 10 to 40 amino acids in length that comprises a structural domain of HCAVIII. This synthesized peptide, coupled to a carrier protein, could be used for generating polyclonal antisera specific for native HCAVIII.

EXAMPLE 4

Production of Antibodies to HCAVIII

The production of polyclonal antisera is described in great detail in Harlow, et al., *Antibodies: A Laboratory Manual*, Cold Spring Harbor Laboratories, New York, 1988 incorporated herein by reference. The HCAVIII protein (SEQ ID NO:4) in the presence of an adjuvant is injected into rabbits with a series of booster shots as a prescribed schedule optimal for high titers of antibody in serum. A total of seven biweekly bleeds were obtained from two rabbits immunized with HCAVIII truncated protein (SEQ ID NO:15). The resulting anti-HCAVIII serum titer was compared to preimmune sera of the same rabbits and determined to be 1000 to 2000-fold greater, hence suitable as a reagent for indirect ELISA (Example 5). Rabbit antibody was partially purified by precipitation with ammonium sulfate (50%, final) followed by dialysis and fractionation by preparative DEAE-HPLC.

An extensive description for producing monoclonal antibodies derived from the spleen B cells of an immunized mouse and a immortalized myeloma cell is found in the above reference for polyclonal antisera production. Mice are immunized with either the purified HCAVIII protein or a glutathione/HCAVIII fusion protein. Following cell fusion, selection for hybrid cells and subcloning, hybridomas are screened for a positive antibody against whole A549 cells or purified HCAVIII protein using an indirect ELISA assay as described for the ELISA kit (see Example 5).

EXAMPLE 5

ELISA Assay of Shed HCAVIII

An indirect ELISA screening assay for HCAVIII protein (SEQ ID NO:4) has been designed to detect and monitor the HCAVIII protein in body fluids including but not limited to serum and other biological fluids such as sputum or bronchial effluxion at effective levels necessary for sensitive but accurate determinations. It is intended to aid in the early diagnosis of non-small cell lung cancer, for which there currently is no effective treatment. An early-detection, accurate, non-invasive assay for non-small cell lung cancer would be of great benefit in the management of this disease.

The immunochemicals used in this procedure were rabbit anti-human HCAVIII antibody (purified IgG, IgM) produced according to the procedure given in Example 4, mouse anti-human HCAVIII (monoclonal) also produced according to the procedure given in Example 4, and goat anti-Rabbit IgG/peroxidase conjugate. The HCAVIII protein standard and internal positive control were produced as described in Example 3 for expression in $E.\ coli$.

Substrate components include 1M $H_2SO_4$ stored at room temperature and 3',5,5'-tetramethylbenzidine (TMB) (Sigma Chemical Co.) used as a peroxidase substrate and stored at room temperature in the dark to prevent exposure to light.

Several buffers, diluents, and blocking agents were used in the procedure. Note that no sodium azide preservative was used in any of the buffers. This was done to avoid any possible interference from the azide with the peroxidase conjugate.

Phosphate buffered saline (PBS) was prepared by adding 32.0 g sodium chloride, 0.8 g potassium phosphate, monobasic, 0.8 g potassium chloride, and 4.6 g sodium phosphate, dibasic, anhydrous, to 3.2 L deionized water and mixing to dissolve. After bringing the solution to 4 L with deionized water and mixing, the pH was about 7.2. The buffer can be stored at 4° C. for a maximum of 3 weeks.

Two bovine serum albumin solutions (BSA) were utilized as diluents. A 1% BSA solution in PBS, utilized as the second antibody/conjugate diluent, was prepared by adding 1 g BSA (bovine albumin, Fraction V, Sigma Chemical Co.) to 80 ml of PBS, allowing it to stand as it slowly goes into solution, adding PBS to a final volume of 100 ml, and then mixing. This diluent can be stored at 4° C. for a maximum of 2 weeks; however if the solution becomes turbid, it should be discarded. As a diluent for the standards and samples, a 0.025% BSA solution in PBS was prepared fresh for each assay by diluting the 1% BSA diluent with PBS 1:40 (vol/vol).

A borate blocking buffer (0.17M $H_3BO_3$, 0.12M NaCl, 0.05% Tween 20, 1 mM EDTA and 0.25% BSA was also used.

The substrate buffer was phosphate-citrate/sodium per borate (Sigma, St. Louis, Mo.).

All assays were performed in Immulon IV plates (Dynatech, Chantilly, Va. #011–010–6301). The assay plates were coated with a monoclonal antibody against HCAVIII by adding 50 ul of a 10 ug/ml solution of antibody in PBS to each well of Immulon IV plates. The plates were covered and incubated overnight at room temperature. The antibody solution was removed and the wells rinsed three times with deionized water. Three-hundred microliters (300 ul) of the borate blocking buffer was added to each well and incubated at room temperature for thirty minutes. The buffer was removed, the wells rinsed three times with deionized water, and the plates air dried. The plates were then wrapped and stored at 4° C.

The standard $E.coli$-derived HCAVIII truncated protein (SEQ ID NO:15), was diluted to 32 ng/ml in PBS/0.025% BSA and two-fold serial dilutions were made in same. The samples were also diluted in PBS/0.025% BSA and 50 ul of standard or sample was applied to each well. The plates were incubated overnight, covered, at room temperature.

The standard and sample solutions were removed from the wells and the wells were rinsed three times with deionized water. Three-hundred microliters (300 ul) borate blocking buffer was added to each well and incubated at room temperature for thirty minutes. The plates were rinsed again with deionized water and tapped (inverted) on paper towels to remove excess water. The second antibody rabbit antisera to HCAVIII truncated protein (SEQ ID NO:15), was diluted to 1 ug/ml in PBS/1% BSA and 50 ul was added to each well. The plates were covered and incubated at room temperature two hours.

The antibody solution was removed from the wells which were then rinsed with deionized water three times. They were then blocked for ten minutes at room temperature with borate blocking buffer, rinsed again with deionied water three times, and tapped on paper towels. The antibody conjugate, goat F(ab')2×rabbit IgG & IgL-HPRO (Tago, Camarillo, Calif.) was diluted 1:16,000 in PBS/1%BSA and 50 ul was added to each well. The plates were covered and incubated at room temperature two hours.

The antibody conjugate solution was removed from the wells and they were rinsed with deionized water three times, blocked with three-hundred ul borate buffer at room temperature then minutes, rinsed three times with deionized water, and tapped on paper towels. The substrate was prepared no more than fifteen minues before use by dissolving one capsule of phosphate-citrate/sodium perborate (Signma, St. Louis, Mo.) in 100 ml water. For each plate, one tablet of TMB was added to 10 ml of the phosphate-citrate/sodium perborate buffer and syringe filtered. One-hundred ul was added to each well and the plates were covered and incubated at room temperature in the dark for one hour. The reaction was stopped by adding 50 ul of 1M $H_2SO_4$ to each well. The plates were read on a Molecular Devices microplate reader at 450nm. Under these conditions, a linear response was obtained from 0.5 to 32 ng/ml using HCAVIII truncated protein as a standard, with the assay sensitivity at 0.5 ng/ml. No cross-reaction was observed against HCAII, an abundant carbonic anhydrase in human serum.

EXAMPLE 6

Carbonic Anhydrase (CA) Activity of Biopsy Tissue

Ice cold solutions of ITB (20 mM imidazole, 5 mM Tris, and 0.4 mM para-nitrophenol, pH 9.4–9.9) and Buffer A (25 mM triethanolamine, 59 mM $H_2SO_4$, and 1 mM benzamidine HCl) are prepared.

A homogenate is prepared by scraping with a cell scraper into 1–2 ml of Buffer A a monolayer of tissue cells cultured from a tissue sample taken from a biopsy. A portion of the sample is then boiled to inactivate CA.

A tube is placed in an ice water bath. For the macroassay, a 10×75 mm glass tubes and rubber stopper with 16 gauge and 18 gauge needle ports is used; for the microassay, a 6×50 mm glass tubes and rubber stopper with 18 gauge needle port and 20 gauge needle with attached PE90 tubing. The sample is added and along with ice cold water to a final volume of 500 μl for macroassay or 50 μl for microassay. 500 μl (macro) or 50 μl (micro) ice cold water is used for a water control. 10 μl antifoam (A. H. Thomas, Philadelphia, Pa.) is added to the tube which is then incubated in ice water for 0.5 to 3 minutes.

The tube is capped with a stopper and $CO_2$ at 150 ml/min (macro) or 100 ml/min (micro) is bubbled through the smaller needle port for 30 sec.

50 μl (macro) or 50 μl (micro) of the ITB solution is rapidly added through the larger needle port with a cold Hamilton syringe. The sample becomes yellow.

Using a timer or stopwatch, the time at which the solution in the tube becomes colorless is measured and recorded. The tube may be momentarily removed from the bath and held in front of a white background to determine the color change. Comparison to a previously acidified sample may be used.

The procedure is repeated with the boiled sample. The volume of sample that corresponds to approximately one enzyme unit is determined using the formula below.

Volume (1EU)=$V_{EU}$=volume used×log2/log (boiled time/activated time) One enzyme unit is the activity that halves the boiled control time.

The assay is repeated 1–3 times with the sample and boiled sample, using the adjusted volume of sample.

---

We claim:

1. An isolated protein comprising a membrane ion and a phosphorylation site comprising the amino acids Arg-Arg-Lys-Ser, said protein further characterized by carbonic anhydrase activity and specificity for expression in non-small cell lung cancer.

2. An isolated protein comprising an amino acid sequence encoded by the coding region of the nucleic acid sequence depicted in SEQ ID NO:1.

3. An isolated protein comprising the amino acid sequence depicted in SEQ ID NO:2.

4. The isolated protein of claim 2 wherein the amino acid sequence is encoded by the coding region from position 19 to position 1093 of SEQ ID NO:1, which is SEQ ID NO:3.

5. An isolated protein comprising the amino acid sequence depicted in SEQ ID NO:4.

6. An isolated protein comprising the amino acid sequence encoded by the coding region of the nucleic acid sequence depicted in SEQ ID NO:12.

7. An isolated protein comprising the amino acid sequence depicted in SEQ ID NO:13.

8. An isolated protein comprising the amino acid sequence encoded by the coding region of the nucleic acid sequence depicted in SEQ ID NO:14.

9. An isolated protein comprising the amino acid sequence depicted in SEQ ID NO:15.

10. An isolated protein possessing specificity for expression in non-small cell lung cancer and a phosphorylation site, said phosphorylation site comprising a sequence selected from the group consisting of: R-Arg-Lys-Ser, Arg-R-Lys-Ser, Arg-Arg-R-Ser, R-R-Lys-Ser, R-R-Lys-R, and Arg-Arg-Lys-R, where R represents an alternate amino acid.

11. The isolated protein of claim 10 wherein the amino acid sequence is encoded by the nucleic acid sequence depicted in SEQ ID NO:17.

12. The isolated protein of claim 10 wherein the amino acid sequence comprises the sequence depicted in SEQ ID NO:18.

* * * * *

UNITED STATES PATENT AND TRADEMARK OFFICE
CERTIFICATE OF CORRECTION

PATENT NO. : 5,773,579
DATED : June 30, 1998
INVENTOR(S) : Richard M. Torczynski, et al.

It is certified that error appears in the above-identified patent and that said Letters Patent is hereby corrected as shown below:

Col. 2, line 7, after "1988", insert --; 101-121--.

Col. 2, line 17, after "1993", insert --; 310-324--.

Col. 2, line 40, after "609", delete --.--.

Col. 2, line 47, after "138:1434-8)", insert --.--.

Col. 2, line 50, before "1994", change "Cancer" to --*Cancer*--.

Col. 2, line 55, change "73:136876" to --73:1368-76--.

Col. 3, line 14, after "UCLA-P3. (", change "Strand" to --Strnad--.

Col. 3, line 42, after "cases of", change "CEA MRNA" to --CEA mRNA--.

Col. 3, line 57, after "demonstrated", change "numerical" to --numerous--.

Col. 3, line 64, before "in situ", change "Fluorescence" to --Fluorescent--.

Col. 3, line 66-67, before "microscopy", change "fluorescence" to --fluorescent--.

Col. 6, line 45, after "evidence", insert --that--.

Col. 6, line 61, after "region" insert --which is--.

Col. 7, line 19, after "region", insert --which is--.

Col. 7, line 19, after "HCAIV", insert --,--.

Col. 7, line 20, after "amino acids", insert --on--.

Col. 7, line 20, after "acids", delete --contained in--.

Col. 7, line 21, after "cell", delete --and--.

Col. 7, line 21, after "cell", insert --, which are--.

Col. 7, line 53, after "radiolabeled with", change "32p" to --$^{32}$P--.

Col. 8, line 37, after "encoding", delete --the--.

Col. 8, line 38, before "is expected", change "MRNA" to --mRNA--.

UNITED STATES PATENT AND TRADEMARK OFFICE
CERTIFICATE OF CORRECTION

PATENT NO. : 5,773,579
DATED : June 30, 1998
INVENTOR(S) : Richard M. Torczynski, et al.

It is certified that error appears in the above-identified patent and that said Letters Patent is hereby corrected as shown below:

Col. 9, line 4, before "be used", insert --to--.

Col. 9, line 39, after "dGTP", change "DATP" to --dATP--.

Col. 10, line 45, change "NO:3" to --NO:1--.

Col. 10, line 45, after "1022", insert --(nucleotide 904 in SEQ ID NO:12)--.

Col. 11, line 4, after "or", insert --an--.

Col. 11, line 40, before "ribonuclease", change "U/ul" to --U/$\mu$l--.

Col. 11, line 42, after "that", delete --then--.

Col. 11, line 44, after "tion of", change "DNAase" to --DNase--.

Col. 11, line 48, after "decreasing", change "concentration" to --concentrations--.

Col. 12, line 56, after "pH 7.5, 10", change "MM" to --mM--.

Col. 13, line 54, after "produced", delete --fused to--.

Col. 13, line 54, after "produced", insert --in which--.

Col. 13, line 55, after "gene", insert --was fused--.

Col. 14, line 1, after "addition", insert --,--.

Col. 14, line 11, after "fragment", change "was" to --were--.

Col. 14, line 18, after "induced in", change "E. Coli" to --E. coli--.

Col. 14, line 22, before "(pH 8.5)", change "Tris.Cl" to --Tris.HCl--.

Col. 14, line 28, after "as", change "a" to --an--.

Col. 14, line 64, after "shots", change "as" to --in--.

UNITED STATES PATENT AND TRADEMARK OFFICE
CERTIFICATE OF CORRECTION

PATENT NO. : 5,773,579
DATED : June 30, 1998
INVENTOR(S) : Richard M. Torczynski, et al.

It is certified that error appears in the above-identified patent and that said Letters Patent is hereby corrected as shown below:

Col. 15, line 10, change "a" to --an--.
Col. 15, line 14, after "cells", insert --,--.
Col. 16, line 4, after "sodium", delete --per--.

Signed and Sealed this

Thirteenth Day of July, 1999

Attest:

Q. TODD DICKINSON

Attesting Officer

Acting Commissioner of Patents and Trademarks

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 1104 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 32..1093

( i x ) FEATURE:
        ( A ) NAME/KEY: mat_peptide
        ( B ) LOCATION: 119..1093

( i x ) FEATURE:
        ( A ) NAME/KEY: misc_feature
        ( B ) LOCATION: 1013..1024
        ( D ) OTHER INFORMATION: /note= "phosphorylation site recognized by protein kinase C and other kina..."

( x i ) SEQUENCE DESCRIPTION: SEQ ID NO:1:

```
GCCGCGCCC  GCCCCGCAGG  AGCCCGCGAA  G  ATG  CCC  CGG  CGC  AGC  CTG  CAC              52
                                      Met  Pro  Arg  Arg  Ser  Leu  His
                                      -29                 -25

GCG  GCG  GCC  GTG  CTC  CTG  CTG  GTG  ATC  TTA  AAG  GAA  CAG  CCT  TCC  AGC      100
Ala  Ala  Ala  Val  Leu  Leu  Leu  Val  Ile  Leu  Lys  Glu  Gln  Pro  Ser  Ser
              -20                      -15                 -10

CCG  GCC  CCA  GTG  AAC  GGT  TCC  AAG  TGG  ACT  TAT  TTT  GGT  CCT  GAT  GGG      148
Pro  Ala  Pro  Val  Asn  Gly  Ser  Lys  Trp  Thr  Tyr  Phe  Gly  Pro  Asp  Gly
     -5                       1                  5                       10

GAG  AAT  AGC  TGG  TCC  AAG  AAG  TAC  CCG  TCG  TGT  GGG  GGC  CTG  CTG  CAG      196
Glu  Asn  Ser  Trp  Ser  Lys  Lys  Tyr  Pro  Ser  Cys  Gly  Gly  Leu  Leu  Gln
                         15                       20                       25

TCC  CCC  ATA  GAC  CTG  CAC  AGT  GAC  ATC  CTC  CAG  TAT  GAC  GCC  AGC  CTC      244
Ser  Pro  Ile  Asp  Leu  His  Ser  Asp  Ile  Leu  Gln  Tyr  Asp  Ala  Ser  Leu
               30                        35                       40
```

| | | | | | | | | | | | | | | | | |
|---|---|---|---|---|---|---|---|---|---|---|---|---|---|---|---|---|
| ACG | CCC | CTC | GAG | TTC | CAA | GGC | TAC | AAT | CTG | TCT | GCC | AAC | AAG | CAG | TTT | 292 |
| Thr | Pro | Leu | Glu | Phe | Gln | Gly | Tyr | Asn | Leu | Ser | Ala | Asn | Lys | Gln | Phe | |
| | | 45 | | | | 50 | | | | | 55 | | | | | |
| CTC | CTG | ACC | AAC | AAT | GGC | CAT | TCA | GTG | AAG | CTG | AAC | CTG | CCC | TCG | GAC | 340 |
| Leu | Leu | Thr | Asn | Asn | Gly | His | Ser | Val | Lys | Leu | Asn | Leu | Pro | Ser | Asp | |
| | 60 | | | | 65 | | | | | 70 | | | | | | |
| ATG | CAC | ATC | CAG | GGC | CTC | CAG | TCT | CGC | TAC | AGT | GCC | ACG | CAG | CTG | CAC | 388 |
| Met | His | Ile | Gln | Gly | Leu | Gln | Ser | Arg | Tyr | Ser | Ala | Thr | Gln | Leu | His | |
| 75 | | | | | 80 | | | | | 85 | | | | | 90 | |
| CTG | CAC | TGG | GGG | AAC | CCG | AAT | GAC | CCG | CAC | GGC | TCT | GAG | CAC | ACC | GTC | 436 |
| Leu | His | Trp | Gly | Asn | Pro | Asn | Asp | Pro | His | Gly | Ser | Glu | His | Thr | Val | |
| | | | | 95 | | | | | 100 | | | | | 105 | | |
| AGC | GGA | CAG | CAC | TTC | GCC | GCC | GAG | CTG | CAC | ATT | GTC | CAT | TAT | AAC | TCA | 484 |
| Ser | Gly | Gln | His | Phe | Ala | Ala | Glu | Leu | His | Ile | Val | His | Tyr | Asn | Ser | |
| | | | 110 | | | | | 115 | | | | | 120 | | | |
| GAC | CTT | TAT | CCT | GAC | GCC | AGC | ACT | GCC | AGC | AAC | AAG | TCA | GAA | GGC | CTC | 532 |
| Asp | Leu | Tyr | Pro | Asp | Ala | Ser | Thr | Ala | Ser | Asn | Lys | Ser | Glu | Gly | Leu | |
| | | 125 | | | | | 130 | | | | | 135 | | | | |
| GCT | GTC | CTG | GCT | GTT | CTC | ATT | GAG | ATG | GGC | TCC | TTC | AAT | CCG | TCC | TAT | 580 |
| Ala | Val | Leu | Ala | Val | Leu | Ile | Glu | Met | Gly | Ser | Phe | Asn | Pro | Ser | Tyr | |
| | 140 | | | | | 145 | | | | | 150 | | | | | |
| GAC | AAG | ATC | TTC | AGT | CAC | CTT | CAA | CAT | GTA | AAG | TAC | AAA | GGC | CAG | GAA | 628 |
| Asp | Lys | Ile | Phe | Ser | His | Leu | Gln | His | Val | Lys | Tyr | Lys | Gly | Gln | Glu | |
| 155 | | | | | 160 | | | | | 165 | | | | | 170 | |
| GCA | TTC | GTC | CCG | GGA | TTC | AAC | ATT | GAA | GAG | CTG | CTT | CCG | GAG | AGG | ACC | 676 |
| Ala | Phe | Val | Pro | Gly | Phe | Asn | Ile | Glu | Glu | Leu | Leu | Pro | Glu | Arg | Thr | |
| | | | | 175 | | | | | 180 | | | | | 185 | | |
| GCT | GAA | TAT | TAC | CGC | TAC | CGG | GGG | TCC | CTG | ACC | ACA | CCC | CCT | TGC | AAC | 724 |
| Ala | Glu | Tyr | Tyr | Arg | Tyr | Arg | Gly | Ser | Leu | Thr | Thr | Pro | Pro | Cys | Asn | |
| | | | 190 | | | | | 195 | | | | | 200 | | | |
| CCC | ACT | GTG | CTC | TGG | ACA | GTT | TTC | CGA | AAC | CCC | GTG | CAA | ATT | TCC | CAG | 772 |
| Pro | Thr | Val | Leu | Trp | Thr | Val | Phe | Arg | Asn | Pro | Val | Gln | Ile | Ser | Gln | |
| | | 205 | | | | | 210 | | | | | 215 | | | | |
| GAG | CAG | CTG | CTG | GCT | TTG | GAG | ACA | GCC | CTG | TAC | TGC | ACA | CAC | ATG | GAC | 820 |
| Glu | Gln | Leu | Leu | Ala | Leu | Glu | Thr | Ala | Leu | Tyr | Cys | Thr | His | Met | Asp | |
| | 220 | | | | | 225 | | | | | 230 | | | | | |
| GAC | CCT | TCC | CCC | AGA | GAA | ATG | ATC | AAC | AAC | TTC | CGG | CAG | GTC | CAG | AAG | 868 |
| Asp | Pro | Ser | Pro | Arg | Glu | Met | Ile | Asn | Asn | Phe | Arg | Gln | Val | Gln | Lys | |
| 235 | | | | | 240 | | | | | 245 | | | | | 250 | |
| TTC | GAT | GAG | AGG | CTG | GTA | TAC | ACC | TCC | TTC | TCC | CAA | GTG | CAA | GTC | TGT | 916 |
| Phe | Asp | Glu | Arg | Leu | Val | Tyr | Thr | Ser | Phe | Ser | Gln | Val | Gln | Val | Cys | |
| | | | | 255 | | | | | 260 | | | | | 265 | | |
| ACT | GCG | GCA | GGA | CTG | AGT | CTG | GGC | ATC | ATC | CTC | TCA | CTG | GCC | CTG | GCT | 964 |
| Thr | Ala | Ala | Gly | Leu | Ser | Leu | Gly | Ile | Ile | Leu | Ser | Leu | Ala | Leu | Ala | |
| | | | 270 | | | | | 275 | | | | | 280 | | | |
| GGC | ATT | CTT | GGC | ATC | TGT | ATT | GTG | GTG | GTG | TCC | ATT | TGG | CTT | TTC | | 1012 |
| Gly | Ile | Leu | Gly | Ile | Cys | Ile | Val | Val | Val | Ser | Ile | Trp | Leu | Phe | | |
| | | 285 | | | | | 290 | | | | | 295 | | | | |
| AGA | AGG | AAG | AGT | ATC | AAA | AAA | GGT | GAT | AAC | AAG | GGA | GTC | ATT | TAC | AAG | 1060 |
| Arg | Arg | Lys | Ser | Ile | Lys | Lys | Gly | Asp | Asn | Lys | Gly | Val | Ile | Tyr | Lys | |
| | | 300 | | | | 305 | | | | | 310 | | | | | |
| CCA | GCC | ACC | AAG | ATG | GAG | ACT | GAG | GCC | CAC | GCT | TGAGGTCCCC G | | | | | 1104 |
| Pro | Ala | Thr | Lys | Met | Glu | Thr | Glu | Ala | His | Ala | | | | | | |
| 315 | | | | 320 | | | | | 325 | | | | | | | |

( 2 ) INFORMATION FOR SEQ ID NO:2:

( i ) SEQUENCE CHARACTERISTICS:
( A ) LENGTH: 354 amino acids
( B ) TYPE: amino acid
( D ) TOPOLOGY: linear (ii) MOLECULE TYPE: protein (xi) SEQUENCE DESCRIPTION: SEQ ID NO:2:

| Met -29 | Pro | Arg | Arg | Ser -25 | Leu | His | Ala | Ala -20 | Ala | Val | Leu | Leu | Leu -15 | Val | Ile |
| Leu | Lys | Glu | Gln -10 | Pro | Ser | Ser | Pro -5 | Ala | Pro | Val | Asn | Gly | Ser 1 | Lys | Trp |
| Thr | Tyr 5 | Phe | Gly | Pro | Asp | Gly 10 | Glu | Asn | Ser | Trp | Ser 15 | Lys | Lys | Tyr | Pro |
| Ser 20 | Cys | Gly | Gly | Leu | Leu 25 | Gln | Ser | Pro | Ile | Leu 30 | His | Ser | Asp | Ile 35 |
| Leu | Gln | Tyr | Asp | Ala 40 | Ser | Leu | Thr | Pro | Leu 45 | Glu | Phe | Gln | Gly | Tyr 50 | Asn |
| Leu | Ser | Ala | Asn 55 | Lys | Gln | Phe | Leu | Leu 60 | Thr | Asn | Asn | Gly | His 65 | Ser | Val |
| Lys | Leu | Asn 70 | Leu | Pro | Ser | Asp | Met 75 | His | Ile | Gln | Gly | Leu 80 | Gln | Ser | Arg |
| Tyr | Ser 85 | Ala | Thr | Gln | Leu | His 90 | Leu | His | Trp | Gly | Asn 95 | Pro | Asn | Asp | Pro |
| His 100 | Gly | Ser | Glu | His | Thr 105 | Val | Ser | Gly | Gln | His 110 | Phe | Ala | Ala | Glu | Leu 115 |
| His | Ile | Val | His | Tyr 120 | Asn | Ser | Asp | Leu | Tyr 125 | Pro | Asp | Ala | Ser | Thr 130 | Ala |
| Ser | Asn | Lys | Ser 135 | Glu | Gly | Leu | Ala | Val 140 | Leu | Ala | Val | Leu | Ile 145 | Glu | Met |
| Gly | Ser | Phe | Asn 150 | Pro | Ser | Tyr | Asp | Lys 155 | Ile | Phe | Ser | His | Leu 160 | Gln | His |
| Val | Lys 165 | Tyr | Lys | Gly | Gln | Glu 170 | Ala | Phe | Val | Pro | Gly 175 | Phe | Asn | Ile | Glu |
| Glu 180 | Leu | Leu | Pro | Glu | Arg 185 | Thr | Ala | Glu | Tyr | Tyr 190 | Arg | Tyr | Arg | Gly | Ser 195 |
| Leu | Thr | Thr | Pro | Pro 200 | Cys | Asn | Pro | Thr | Val 205 | Leu | Trp | Thr | Val | Phe 210 | Arg |
| Asn | Pro | Val | Gln 215 | Ile | Ser | Gln | Glu | Gln 220 | Leu | Leu | Ala | Leu | Glu 225 | Thr | Ala |
| Leu | Tyr | Cys 230 | Thr | His | Met | Asp | Asp 235 | Pro | Ser | Pro | Arg | Glu 240 | Met | Ile | Asn |
| Asn | Phe 245 | Arg | Gln | Val | Gln | Lys 250 | Phe | Asp | Glu | Arg | Leu 255 | Val | Tyr | Thr | Ser |
| Phe 260 | Ser | Gln | Val | Gln | Val 265 | Cys | Thr | Ala | Ala | Gly 270 | Leu | Ser | Leu | Gly | Ile 275 |
| Ile | Leu | Ser | Leu | Ala 280 | Leu | Ala | Gly | Ile | Leu 285 | Gly | Ile | Cys | Ile | Val 290 | Val |
| Val | Val | Ser | Ile 295 | Trp | Leu | Phe | Arg | Arg 300 | Lys | Ser | Ile | Lys | Lys 305 | Gly | Asp |
| Asn | Lys | Gly 310 | Val | Ile | Tyr | Lys | Pro 315 | Ala | Thr | Lys | Met | Glu 320 | Thr | Glu | Ala |
| His | Ala 325 | | | | | | | | | | | | | | |

(2) INFORMATION FOR SEQ ID NO:3:

(i) SEQUENCE CHARACTERISTICS:
(A) LENGTH: 986 base pairs
(B) TYPE: nucleic acid (  C  ) STRANDEDNESS: both
(  D  ) TOPOLOGY: linear (  i i  ) MOLECULE TYPE: cDNA (  i x  ) FEATURE:
(  A  ) NAME/KEY: CDS
(  B  ) LOCATION: 1..975

(  i x  ) FEATURE:
(  A  ) NAME/KEY: misc_feature
(  B  ) LOCATION: 895..906
(  D  ) OTHER INFORMATION: /note= "phosphorylation site recognized by protein C kinase and other kina..."

(  x i  ) SEQUENCE DESCRIPTION: SEQ ID NO:3:

| TCC | AAG | TGG | ACT | TAT | TTT | GGT | CCT | GAT | GGG | GAG | AAT | AGC | TGG | TCC | AAG | 48 |
| Ser | Lys | Trp | Thr | Tyr | Phe | Gly | Pro | Asp | Gly | Glu | Asn | Ser | Trp | Ser | Lys | |
| 1 | | | | 5 | | | | | 10 | | | | | 15 | | |

| AAG | TAC | CCG | TCG | TGT | GGG | GGC | CTG | CTG | CAG | TCC | CCC | ATA | GAC | CTG | CAC | 96 |
| Lys | Tyr | Pro | Ser | Cys | Gly | Gly | Leu | Leu | Gln | Ser | Pro | Ile | Asp | Leu | His | |
| | | | 20 | | | | | 25 | | | | | 30 | | | |

| AGT | GAC | ATC | CTC | CAG | TAT | GAC | GCC | AGC | CTC | ACG | CCC | CTC | GAG | TTC | CAA | 144 |
| Ser | Asp | Ile | Leu | Gln | Tyr | Asp | Ala | Ser | Leu | Thr | Pro | Leu | Glu | Phe | Gln | |
| | | 35 | | | | | 40 | | | | | 45 | | | | |

| GGC | TAC | AAT | CTG | TCT | GCC | AAC | AAG | CAG | TTT | CTC | CTG | ACC | AAC | AAT | GGC | 192 |
| Gly | Tyr | Asn | Leu | Ser | Ala | Asn | Lys | Gln | Phe | Leu | Leu | Thr | Asn | Asn | Gly | |
| | 50 | | | | | 55 | | | | | 60 | | | | | |

| CAT | TCA | GTG | AAG | CTG | AAC | CTG | CCC | TCG | GAC | ATG | CAC | ATC | CAG | GGC | CTC | 240 |
| His | Ser | Val | Lys | Leu | Asn | Leu | Pro | Ser | Asp | Met | His | Ile | Gln | Gly | Leu | |
| 65 | | | | | 70 | | | | | 75 | | | | | 80 | |

| CAG | TCT | CGC | TAC | AGT | GCC | ACG | CAG | CTG | CAC | CTG | CAC | TGG | GGG | AAC | CCG | 288 |
| Gln | Ser | Arg | Tyr | Ser | Ala | Thr | Gln | Leu | His | Leu | His | Trp | Gly | Asn | Pro | |
| | | | | 85 | | | | | 90 | | | | | 95 | | |

| AAT | GAC | CCG | CAC | GGC | TCT | GAG | CAC | ACC | GTC | AGC | GGA | CAG | CAC | TTC | GCC | 336 |
| Asn | Asp | Pro | His | Gly | Ser | Glu | His | Thr | Val | Ser | Gly | Gln | His | Phe | Ala | |
| | | | 100 | | | | | 105 | | | | | 110 | | | |

| GCC | GAG | CTG | CAC | ATT | GTC | CAT | TAT | AAC | TCA | GAC | CTT | TAT | CCT | GAC | GCC | 384 |
| Ala | Glu | Leu | His | Ile | Val | His | Tyr | Asn | Ser | Asp | Leu | Tyr | Pro | Asp | Ala | |
| | | | 115 | | | | 120 | | | | | 125 | | | | |

| AGC | ACT | GCC | AGC | AAC | AAG | TCA | GAA | GGC | CTC | GCT | GTC | CTG | GCT | GTT | CTC | 432 |
| Ser | Thr | Ala | Ser | Asn | Lys | Ser | Glu | Gly | Leu | Ala | Val | Leu | Ala | Val | Leu | |
| | 130 | | | | | 135 | | | | | 140 | | | | | |

| ATT | GAG | ATG | GGC | TCC | TTC | AAT | CCG | TCC | TAT | GAC | AAG | ATC | TTC | AGT | CAC | 480 |
| Ile | Glu | Met | Gly | Ser | Phe | Asn | Pro | Ser | Tyr | Asp | Lys | Ile | Phe | Ser | His | |
| 145 | | | | | 150 | | | | | 155 | | | | | 160 | |

| CTT | CAA | CAT | GTA | AAG | TAC | AAA | GGC | CAG | GAA | GCA | TTC | GTC | CCG | GGA | TTC | 528 |
| Leu | Gln | His | Val | Lys | Tyr | Lys | Gly | Gln | Glu | Ala | Phe | Val | Pro | Gly | Phe | |
| | | | | 165 | | | | | 170 | | | | | 175 | | |

| AAC | ATT | GAA | GAG | CTG | CTT | CCG | GAG | AGG | ACC | GCT | GAA | TAT | TAC | CGC | TAC | 576 |
| Asn | Ile | Glu | Glu | Leu | Leu | Pro | Glu | Arg | Thr | Ala | Glu | Tyr | Tyr | Arg | Tyr | |
| | | | 180 | | | | | 185 | | | | | 190 | | | |

| CGG | GGG | TCC | CTG | ACC | ACA | CCC | CCT | TGC | AAC | CCC | ACT | GTG | CTC | TGG | ACA | 624 |
| Arg | Gly | Ser | Leu | Thr | Thr | Pro | Pro | Cys | Asn | Pro | Thr | Val | Leu | Trp | Thr | |
| | | 195 | | | | | 200 | | | | | 205 | | | | |

| GTT | TTC | CGA | AAC | CCC | GTG | CAA | ATT | TCC | CAG | GAG | CAG | CTG | CTG | GCT | TTG | 672 |
| Val | Phe | Arg | Asn | Pro | Val | Gln | Ile | Ser | Gln | Glu | Gln | Leu | Leu | Ala | Leu | |
| | 210 | | | | | 215 | | | | | 220 | | | | | |

| GAG | ACA | GCC | CTG | TAC | TGC | ACA | CAC | ATG | GAC | GAC | CCT | TCC | CCC | AGA | GAA | 720 |
| Glu | Thr | Ala | Leu | Tyr | Cys | Thr | His | Met | Asp | Asp | Pro | Ser | Pro | Arg | Glu | |
| 225 | | | | | 230 | | | | | 235 | | | | | 240 | |

| ATG | ATC | AAC | AAC | TTC | CGG | CAG | GTC | CAG | AAG | TTC | GAT | GAG | AGG | CTG | GTA | 768 |
| Met | Ile | Asn | Asn | Phe | Arg | Gln | Val | Gln | Lys | Phe | Asp | Glu | Arg | Leu | Val | |
| | | | | 245 | | | | | 250 | | | | | 255 | | |

| | | | | | | | | | | | | | | | | |
|---|---|---|---|---|---|---|---|---|---|---|---|---|---|---|---|---|
| TAC | ACC | TCC | TTC | TCC | CAA | GTG | CAA | GTC | TGT | ACT | GCG | GCA | GGA | CTG | AGT | 816 |
| Tyr | Thr | Ser | Phe 260 | Ser | Gln | Val | Gln 265 | Val | Cys | Thr | Ala | Ala | Gly 270 | Leu | Ser | |
| CTG | GGC | ATC | ATC | CTC | TCA | CTG | GCC | CTG | GCT | GGC | ATT | CTT | GGC | ATC | TGT | 864 |
| Leu | Gly | Ile 275 | Ile | Leu | Ser | Leu | Ala 280 | Leu | Ala | Gly | Ile | Leu 285 | Gly | Ile | Cys | |
| ATT | GTG | GTG | GTG | GTG | TCC | ATT | TGG | CTT | TTC | AGA | AGG | AAG | AGT | ATC | AAA | 912 |
| Ile | Val 290 | Val | Val | Val | Ser | Ile 295 | Trp | Leu | Phe | Arg | Arg 300 | Lys | Ser | Ile | Lys | |
| AAA | GGT | GAT | AAC | AAG | GGA | GTC | ATT | TAC | AAG | CCA | GCC | ACC | AAG | ATG | GAG | 960 |
| Lys 305 | Gly | Asp | Asn | Lys | Gly 310 | Val | Ile | Tyr | Lys | Pro 315 | Ala | Thr | Lys | Met | Glu 320 | |
| ACT | GAG | GCC | CAC | GCT | TGAGGTCCCC G | | | | | | | | | | | 986 |
| Thr | Glu | Ala | His | Ala 325 | | | | | | | | | | | | |

(2) INFORMATION FOR SEQ ID NO:4:

(i) SEQUENCE CHARACTERISTICS:
        (A) LENGTH: 325 amino acids
        (B) TYPE: amino acid
        (D) TOPOLOGY: linear (ii) MOLECULE TYPE: protein (xi) SEQUENCE DESCRIPTION: SEQ ID NO:4:

| | | | | | | | | | | | | | | |
|---|---|---|---|---|---|---|---|---|---|---|---|---|---|---|
| Ser 1 | Lys | Trp | Thr | Tyr 5 | Phe | Gly | Pro | Asp | Gly 10 | Glu | Asn | Ser | Trp | Ser Lys 15 |
| Lys | Tyr | Pro | Ser 20 | Cys | Gly | Gly | Leu | Leu 25 | Gln | Ser | Pro | Ile | Asp 30 | Leu His |
| Ser | Asp | Ile 35 | Leu | Gln | Tyr | Asp | Ala 40 | Ser | Leu | Thr | Pro | Leu 45 | Glu | Phe Gln |
| Gly | Tyr 50 | Asn | Leu | Ser | Ala | Asn 55 | Lys | Gln | Phe | Leu | Leu 60 | Thr | Asn | Asn Gly |
| His 65 | Ser | Val | Lys | Leu | Asn 70 | Leu | Pro | Ser | Asp | Met 75 | His | Ile | Gln | Gly Leu 80 |
| Gln | Ser | Arg | Tyr | Ser 85 | Ala | Thr | Gln | Leu | His 90 | Leu | His | Trp | Gly | Asn Pro 95 |
| Asn | Asp | Pro | His 100 | Gly | Ser | Glu | His | Thr 105 | Val | Ser | Gly | Gln | His 110 | Phe Ala |
| Ala | Glu | Leu 115 | His | Ile | Val | His | Tyr 120 | Asn | Ser | Asp | Leu | Tyr 125 | Pro | Asp Ala |
| Ser | Thr 130 | Ala | Ser | Asn | Lys | Ser 135 | Glu | Gly | Leu | Ala | Val 140 | Leu | Ala | Val Leu |
| Ile 145 | Glu | Met | Gly | Ser | Phe 150 | Asn | Pro | Ser | Tyr | Asp 155 | Lys | Ile | Phe | Ser His 160 |
| Leu | Gln | His | Val | Lys 165 | Tyr | Lys | Gly | Gln | Glu 170 | Ala | Phe | Val | Pro | Gly Phe 175 |
| Asn | Ile | Glu | Glu 180 | Leu | Leu | Pro | Glu | Arg 185 | Thr | Ala | Glu | Tyr | Tyr 190 | Arg Tyr |
| Arg | Gly | Ser 195 | Leu | Thr | Thr | Pro | Pro 200 | Cys | Asn | Pro | Thr | Val 205 | Leu | Trp Thr |
| Val | Phe 210 | Arg | Asn | Pro | Val | Gln 215 | Ile | Ser | Gln | Glu | Gln 220 | Leu | Leu | Ala Leu |
| Glu 225 | Thr | Ala | Leu | Tyr | Cys 230 | Thr | His | Met | Asp | Asp 235 | Pro | Ser | Pro | Arg Glu 240 |
| Met | Ile | Asn | Asn | Phe 245 | Arg | Gln | Val | Gln | Lys 250 | Phe | Asp | Glu | Arg | Leu Val 255 |

| | | | | | | | | | | | | | | |
|---|---|---|---|---|---|---|---|---|---|---|---|---|---|---|
|Tyr|Thr|Ser|Phe 260|Ser|Gln|Val|Gln 265|Cys|Thr|Ala|Ala|Gly 270|Leu|Ser|
|Leu|Gly|Ile 275|Ile|Leu|Ser|Leu 280|Ala|Leu|Ala|Gly|Ile 285|Leu|Gly|Ile|Cys|
|Ile|Val 290|Val|Val|Val|Ser 295|Ile|Trp|Leu|Phe|Arg 300|Arg|Lys|Ser|Ile|Lys|
|Lys 305|Gly|Asp|Asn|Lys|Gly 310|Val|Ile|Tyr|Lys|Pro 315|Ala|Thr|Lys|Met|Glu 320|
|Thr|Glu|Ala|His|Ala 325| | | | | | | | | | | |

( 2 ) INFORMATION FOR SEQ ID NO:5:

( i ) SEQUENCE CHARACTERISTICS:
        ( A ) LENGTH: 2134 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 116..1177

( i x ) FEATURE:
        ( A ) NAME/KEY: mat_peptide
        ( B ) LOCATION: 203..1177

( x i ) SEQUENCE DESCRIPTION: SEQ ID NO:5:

| | | | | | | |
|---|---|---|---|---|---|---|
|GTACTCGCCA|CGGCACCCAG|GCTGCGCGCA|CGCGGTCCCG|GTGTGCAGCT|GGAGAGCGAG|60|
|CGGCCACCGG|GAGCCCCGG|CACAGCCCGC|GCCCGCCCCG|CAGGAGCCCG|CGAAG ATG<br>                        Met<br>                        - 29|118|

| | | | | | | | | | | | | | | | |
|---|---|---|---|---|---|---|---|---|---|---|---|---|---|---|---|
|CCC|CGG|CGC|AGC|CTG|CAC|GCG|GCG|GCC|GTG|CTC|CTG|CTG|GTG|ATC|TTA|166|
|Pro|Arg|Arg|Ser<br>- 25|Leu|His|Ala|Ala|Ala<br>- 20|Val|Leu|Leu|Leu|Val<br>- 15|Ile|Leu| |
|AAG|GAA|CAG|CCT|TCC|AGC|CCG|GCC|CCA|GTG|AAC|GGT|TCC|AAG|TGG|ACT|214|
|Lys|Glu|Gln<br>- 10|Pro|Ser|Ser|Pro|Ala<br>- 5|Pro|Val|Asn|Gly|Ser|Lys<br>1|Trp|Thr| |
|TAT|TTT|GGT|CCT|GAT|GGG|GAG|AAT|AGC|TGG|TCC|AAG|AAG|TAC|CCG|TCG|262|
|Tyr|Phe<br>5|Gly|Pro|Asp|Gly<br>10|Glu|Asn|Ser|Trp|Ser<br>15|Lys|Lys|Tyr|Pro|Ser<br>20| |
|TGT|GGG|GGC|CTG|CTG|CAG|TCC|CCC|ATA|GAC|CTG|CAC|AGT|GAC|ATC|CTC|310|
|Cys|Gly|Gly|Leu|Leu<br>25|Gln|Ser|Pro|Ile|Asp<br>30|Leu|His|Ser|Asp|Ile<br>35|Leu| |
|CAG|TAT|GAC|GCC|AGC|CTC|ACG|CCC|CTC|GAG|TTC|CAA|GGC|TAC|AAT|CTG|358|
|Gln|Tyr|Asp|Ala<br>40|Ser|Leu|Thr|Pro|Leu<br>45|Glu|Phe|Gln|Gly|Tyr<br>50|Asn|Leu| |
|TCT|GCC|AAC|AAG|CAG|TTT|CTC|CTG|ACC|AAC|AAT|GGC|CAT|TCA|GTG|AAG|406|
|Ser|Ala|Asn|Lys<br>55|Gln|Phe|Leu|Leu|Thr<br>60|Asn|Asn|Gly|His|Ser<br>65|Val|Lys| |
|CTG|AAC|CTG|CCC|TCG|GAC|ATG|CAC|ATC|CAG|GGC|CTC|CAG|TCT|CGC|TAC|454|
|Leu|Asn|Leu<br>70|Pro|Ser|Asp|Met|His<br>75|Ile|Gln|Gly|Leu|Gln<br>80|Ser|Arg|Tyr| |
|AGT|GCC|ACG|CAG|CTG|CAC|CTG|CAC|TGG|GGG|AAC|CCG|AAT|GAC|CCG|CAC|502|
|Ser|Ala<br>85|Thr|Gln|Leu|His<br>90|Leu|His|Trp|Gly|Asn<br>95|Pro|Asn|Asp|Pro|His<br>100| |
|GGC|TCT|GAG|CAC|ACC|GTC|AGC|GGA|CAG|CAC|TTC|GCC|GCC|GAG|CTG|CAC|550|
|Gly|Ser|Glu|His<br>105|Thr|Val|Ser|Gly|Gln<br>110|His|Phe|Ala|Ala|Glu<br>115|Leu|His| |
|ATT|GTC|CAT|TAT|AAC|TCA|GAC|CTT|TAT|CCT|GAC|GCC|AGC|ACT|GCC|AGC|598|

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| Ile   | Val   | His   | Tyr   | Asn   | Ser   | Asp   | Leu   | Tyr   | Pro   | Asp   | Ala   | Ser   | Thr   | Ala   | Ser   |      |
|       |       |       | 120   |       |       |       |       | 125   |       |       |       |       | 130   |       |       |      |
| AAC   | AAG   | TCA   | GAA   | GGC   | CTC   | GCT   | GTC   | CTG   | GCT   | GTT   | CTC   | ATT   | GAG   | ATG   | GGC   | 646  |
| Asn   | Lys   | Ser   | Glu   | Gly   | Leu   | Ala   | Val   | Leu   | Ala   | Val   | Leu   | Ile   | Glu   | Met   | Gly   |      |
|       |       | 135   |       |       |       |       | 140   |       |       |       |       | 145   |       |       |       |      |
| TCC   | TTC   | AAT   | CCG   | TCC   | TAT   | GAC   | AAG   | ATC   | TTC   | AGT   | CAC   | CTT   | CAA   | CAT   | GTA   | 694  |
| Ser   | Phe   | Asn   | Pro   | Ser   | Tyr   | Asp   | Lys   | Ile   | Phe   | Ser   | His   | Leu   | Gln   | His   | Val   |      |
|       | 150   |       |       |       |       | 155   |       |       |       |       | 160   |       |       |       |       |      |
| AAG   | TAC   | AAA   | GGC   | CAG   | GAA   | GCA   | TTC   | GTC   | CCG   | GGA   | TTC   | AAC   | ATT   | GAA   | GAG   | 742  |
| Lys   | Tyr   | Lys   | Gly   | Gln   | Glu   | Ala   | Phe   | Val   | Pro   | Gly   | Phe   | Asn   | Ile   | Glu   | Glu   |      |
| 165   |       |       |       |       | 170   |       |       |       |       | 175   |       |       |       |       | 180   |      |
| CTG   | CTT   | CCG   | GAG   | AGG   | ACC   | GCT   | GAA   | TAT   | TAC   | CGC   | TAC   | CGG   | GGG   | TCC   | CTG   | 790  |
| Leu   | Leu   | Pro   | Glu   | Arg   | Thr   | Ala   | Glu   | Tyr   | Tyr   | Arg   | Tyr   | Arg   | Gly   | Ser   | Leu   |      |
|       |       |       |       | 185   |       |       |       |       | 190   |       |       |       |       | 195   |       |      |
| ACC   | ACA   | CCC   | CCT   | TGC   | AAC   | CCC   | ACT   | GTG   | CTC   | TGG   | ACA   | GTT   | TTC   | CGA   | AAC   | 838  |
| Thr   | Thr   | Pro   | Pro   | Cys   | Asn   | Pro   | Thr   | Val   | Leu   | Trp   | Thr   | Val   | Phe   | Arg   | Asn   |      |
|       |       |       | 200   |       |       |       |       | 205   |       |       |       |       | 210   |       |       |      |
| CCC   | GTG   | CAA   | ATT   | TCC   | CAG   | GAG   | CAG   | CTG   | CTG   | GCT   | TTG   | GAG   | ACA   | GCC   | CTG   | 886  |
| Pro   | Val   | Gln   | Ile   | Ser   | Gln   | Glu   | Gln   | Leu   | Leu   | Ala   | Leu   | Glu   | Thr   | Ala   | Leu   |      |
|       |       | 215   |       |       |       |       | 220   |       |       |       |       | 225   |       |       |       |      |
| TAC   | TGC   | ACA   | CAC   | ATG   | GAC   | GAC   | CCT   | TCC   | CCC   | AGA   | GAA   | ATG   | ATC   | AAC   | AAC   | 934  |
| Tyr   | Cys   | Thr   | His   | Met   | Asp   | Asp   | Pro   | Ser   | Pro   | Arg   | Glu   | Met   | Ile   | Asn   | Asn   |      |
|       | 230   |       |       |       |       | 235   |       |       |       |       | 240   |       |       |       |       |      |
| TTC   | CGG   | CAG   | GTC   | CAG   | AAG   | TTC   | GAT   | GAG   | AGG   | CTG   | GTA   | TAC   | ACC   | TCC   | TTC   | 982  |
| Phe   | Arg   | Gln   | Val   | Gln   | Lys   | Phe   | Asp   | Glu   | Arg   | Leu   | Val   | Tyr   | Thr   | Ser   | Phe   |      |
| 245   |       |       |       |       | 250   |       |       |       |       | 255   |       |       |       |       | 260   |      |
| TCC   | CAA   | GTG   | CAA   | GTC   | TGT   | ACT   | GCG   | GCA   | GGA   | CTG   | AGT   | CTG   | GGC   | ATC   | ATC   | 1030 |
| Ser   | Gln   | Val   | Gln   | Val   | Cys   | Thr   | Ala   | Ala   | Gly   | Leu   | Ser   | Leu   | Gly   | Ile   | Ile   |      |
|       |       |       |       | 265   |       |       |       |       | 270   |       |       |       |       | 275   |       |      |
| CTC   | TCA   | CTG   | GCC   | CTG   | GCT   | GGC   | ATT   | CTT   | GGC   | ATC   | TGT   | ATT   | GTG   | GTG   | GTG   | 1078 |
| Leu   | Ser   | Leu   | Ala   | Leu   | Ala   | Gly   | Ile   | Leu   | Gly   | Ile   | Cys   | Ile   | Val   | Val   | Val   |      |
|       |       |       | 280   |       |       |       |       | 285   |       |       |       |       | 290   |       |       |      |
| GTG   | TCC   | ATT   | TGG   | CTT   | TTC   | AGA   | AGG   | AAG   | AGT   | ATC   | AAA   | AAA   | GGT   | GAT   | AAC   | 1126 |
| Val   | Ser   | Ile   | Trp   | Leu   | Phe   | Arg   | Arg   | Lys   | Ser   | Ile   | Lys   | Lys   | Gly   | Asp   | Asn   |      |
|       |       | 295   |       |       |       |       | 300   |       |       |       |       | 305   |       |       |       |      |
| AAG   | GGA   | GTC   | ATT   | TAC   | AAG   | CCA   | GCC   | ACC   | AAG   | ATG   | GAG   | ACT   | GAG   | GCC   | CAC   | 1174 |
| Lys   | Gly   | Val   | Ile   | Tyr   | Lys   | Pro   | Ala   | Thr   | Lys   | Met   | Glu   | Thr   | Glu   | Ala   | His   |      |
|       | 310   |       |       |       |       | 315   |       |       |       |       | 320   |       |       |       |       |      |
| GCT   | TGAGGTCCCC | GGAGCTCCCG | GCACATCCA | GGAAGGACCT | TGCTTTGGAC |   |   |   |   |   |   |   |   |   |   | 1227 |
| Ala   |       |       |       |       |       |       |       |       |       |       |       |       |       |       |       |      |
| 325   |       |       |       |       |       |       |       |       |       |       |       |       |       |       |       |      |

| | | | | |
|---|---|---|---|---|
| CCTACACACT | TCGGCTCTCT | GGACACTTGC | GACACCTCAA | GGTGTTCTCT | GTAGCTCAAT | 1287 |
| CTGCAAACAT | GCCAGGCCTC | AGGGATCCTC | TGCTGGGTGC | CTCCTTGCCT | TGGGACCATG | 1347 |
| GCCACCCCAG | AGCCATCCGA | TCGATGGATG | GGATGCACTC | TCAGACCAAG | CAGCAGGAAT | 1407 |
| TCAAAGCTGC | TTGCTGTAAC | TGTGTGAGAT | TGTGAAGTGG | TCTGAATTCT | GGAATCACAA | 1467 |
| ACCAAGCCAT | GCTGGTGGGC | CATTAATGGT | TGGAAAACAC | TTTCATCCGG | GGCTTTGCCA | 1527 |
| GAGCGTGCTT | TCAAGTGTCC | TGGAAATTCT | GCTGCTTCTC | CAAGCTTTCA | GACAAGAATG | 1587 |
| TGCACTCTCT | GCTTAGGTTT | TGCTTGGGAA | ACTCAACTTC | TTTCCTCTGG | AGACGGGGCA | 1647 |
| TCTCCCTCTG | ATTTCCTTCT | GCTATGACAA | AACCTTTAAT | CTGCACCTTA | CAACTCGGGG | 1707 |
| ACAAATGGGG | ACAGGAAGGA | TCAAGTTGTA | GAGAGAAAAA | GAAAACAAGA | GATATACATT | 1767 |
| GTGATATATT | AGGGACACTT | TCACAGTCCT | GTCCTCTGGA | TCACAGACAC | TGCACAGACC | 1827 |
| TTAGGGAATG | GCAGGTTCAA | GTTCCACTTC | TTGGTGGGGA | TGAGAAGGGA | GAGAGAGCTA | 1887 |
| GAGGGACAAA | GAGAATGAGA | AGACATGGAT | GATCTGGGAG | AGTCTCACTT | TGGAATCAGA | 1947 |
| ATTGGAATCA | CATTCTGTTT | ATCAAGCCAT | AATGTAAGGA | CAGAATAATA | CAATATTAAG | 2007 |

```
TCCAAATCCA ACCTCCTGTC AGTGGAGCAG TTATGTTTTA TACTCTACAG ATTTTACAAA      2067

TAATGAGGCT GTTCCTTGAA AATGTGTTGT TGCTGTGTCC TGGAGGAGAC ATGAGTTCCG      2127

AGATGAC                                                                2134
```

( 2 ) INFORMATION FOR SEQ ID NO:6:

( i ) SEQUENCE CHARACTERISTICS:
        ( A ) LENGTH: 354 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Pro  Arg  Arg  Ser  Leu  His  Ala  Ala  Ala  Val  Leu  Leu  Leu  Val  Ile
-29            -25                      -20                      -15

Leu  Lys  Glu  Gln  Pro  Ser  Ser  Pro  Ala  Pro  Val  Asn  Gly  Ser  Lys  Trp
               -10                       -5                        1

Thr  Tyr  Phe  Gly  Pro  Asp  Gly  Glu  Asn  Ser  Trp  Ser  Lys  Lys  Tyr  Pro
          5                   10                       15

Ser  Cys  Gly  Gly  Leu  Leu  Gln  Ser  Pro  Ile  Asp  Leu  His  Ser  Asp  Ile
20                       25                      30                            35

Leu  Gln  Tyr  Asp  Ala  Ser  Leu  Thr  Pro  Leu  Glu  Phe  Gln  Gly  Tyr  Asn
               40                      45                            50

Leu  Ser  Ala  Asn  Lys  Gln  Phe  Leu  Leu  Thr  Asn  Asn  Gly  His  Ser  Val
               55                      60                            65

Lys  Leu  Asn  Leu  Pro  Ser  Asp  Met  His  Ile  Gln  Gly  Leu  Gln  Ser  Arg
          70                       75                      80

Tyr  Ser  Ala  Thr  Gln  Leu  His  Leu  His  Trp  Gly  Asn  Pro  Asn  Asp  Pro
     85                       90                       95

His  Gly  Ser  Glu  His  Thr  Val  Ser  Gly  Gln  His  Phe  Ala  Ala  Glu  Leu
100                      105                      110                      115

His  Ile  Val  His  Tyr  Asn  Ser  Asp  Leu  Tyr  Pro  Asp  Ala  Ser  Thr  Ala
                    120                      125                      130

Ser  Asn  Lys  Ser  Glu  Gly  Leu  Ala  Val  Leu  Ala  Val  Leu  Ile  Glu  Met
               135                      140                      145

Gly  Ser  Phe  Asn  Pro  Ser  Tyr  Asp  Lys  Ile  Phe  Ser  His  Leu  Gln  His
          150                      155                      160

Val  Lys  Tyr  Lys  Gly  Gln  Glu  Ala  Phe  Val  Pro  Gly  Phe  Asn  Ile  Glu
     165                      170                      175

Glu  Leu  Leu  Pro  Glu  Arg  Thr  Ala  Glu  Tyr  Tyr  Arg  Tyr  Arg  Gly  Ser
180                      185                      190                      195

Leu  Thr  Thr  Pro  Pro  Cys  Asn  Pro  Thr  Val  Leu  Trp  Thr  Val  Phe  Arg
               200                      205                      210

Asn  Pro  Val  Gln  Ile  Ser  Gln  Glu  Gln  Leu  Leu  Ala  Leu  Glu  Thr  Ala
               215                      220                      225

Leu  Tyr  Cys  Thr  His  Met  Asp  Asp  Pro  Ser  Pro  Arg  Glu  Met  Ile  Asn
          230                      235                      240

Asn  Phe  Arg  Gln  Val  Gln  Lys  Phe  Asp  Glu  Arg  Leu  Val  Tyr  Thr  Ser
     245                      250                      255

Phe  Ser  Gln  Val  Gln  Val  Cys  Thr  Ala  Ala  Gly  Leu  Ser  Leu  Gly  Ile
260                      265                      270                      275

Ile  Leu  Ser  Leu  Ala  Leu  Ala  Gly  Ile  Leu  Gly  Ile  Cys  Ile  Val  Val
               280                      285                      290

Val  Val  Ser  Ile  Trp  Leu  Phe  Arg  Arg  Lys  Ser  Ile  Lys  Lys  Gly  Asp
```

| | 295 | | | | 300 | | | | 305 | | | |
|---|---|---|---|---|---|---|---|---|---|---|---|---|
| Asn | Lys | Gly | Val | Ile | Tyr | Lys | Pro | Ala | Thr | Lys | Met | Glu | Thr | Glu | Ala |
| | | 310 | | | | | 315 | | | | | 320 | | | |

His Ala
    325

(2) INFORMATION FOR SEQ ID NO:7:

(i) SEQUENCE CHARACTERISTICS:
        (A) LENGTH: 624 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:7:

```
CCAATCTGCC  TTTGAATCTG  GAGGAAATAG  GCAGAAACAA  AATGACTGTA  GAACTTATTC     60
TCTGTAGGCC  AAATTTCATT  TCAGCCACTT  CTGCAGGATC  CCTACTGCCA  ACCTGGAATG    120
GAGACTTTTA  TCTACTTCTC  TCTCTCTGAA  GATGTCAAAT  CGTGGTTTAG  ATCAAATATA    180
TTTCAAGCTA  TAAAAGCAGG  AGGTTATCTG  TGCAGGGGGC  TGGCATCATG  TATTTAGGGG    240
CAAGTAATAA  TGGAATGCTA  CTAAGATACT  CCATATTCTT  CCCCGAATCA  CACAGACAGT    300
TTCTGACAGG  CGCAACTCCT  CCATTTTCCT  CCCGCAGGTG  AGAACCCTGT  GGAGATGAGT    360
CAGTGCCATG  ACTGAGAAGG  AACCGACCCC  TAGTTGAGAG  CACCTTGCAG  TTCCCCGAGA    420
ACTTTCTGAT  TCACAGTCTC  ATTTTGACAG  CATGAAATGT  CCTCTTGAAG  CATAGCTTTT    480
TAAATATCTT  TTTCCTTCTA  CTCCTCCCTC  TGACTCTAAG  AATTCTCTCT  TCTGGAATCG    540
CTTGAACCCA  GGAGGCGGAG  GTTGCAGTAA  GCCAAGGTCA  TGCCACTGCA  CTCTAGCCTG    600
GGTGACAGAG  CGAGACTCCA  TCTC                                             624
```

(2) INFORMATION FOR SEQ ID NO:8:

(i) SEQUENCE CHARACTERISTICS:
        (A) LENGTH: 12 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 1..12

(xi) SEQUENCE DESCRIPTION: SEQ ID NO:8:

```
AGA  AGG  AAG  AGT                                                        12
Arg  Arg  Lys  Ser
```

(2) INFORMATION FOR SEQ ID NO:9:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO:9:

Arg  Arg  Lys  Ser (2) INFORMATION FOR SEQ ID NO:10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

TGAGTCGACG          10

(2) INFORMATION FOR SEQ ID NO:11:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

AATTCGTCGA CTCA        14

(2) INFORMATION FOR SEQ ID NO:12:

(i) SEQUENCE CHARACTERISTICS:
        (A) LENGTH: 813 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..813

(xi) SEQUENCE DESCRIPTION: SEQ ID NO:12:

```
TCC  AAG  TGG  ACT  TAT  TTT  GGT  CCT  GAT  GGG  GAG  AAT  AGC  TGG  TCC  AAG     48
Ser  Lys  Trp  Thr  Tyr  Phe  Gly  Pro  Asp  Gly  Glu  Asn  Ser  Trp  Ser  Lys
 1              5                        10                       15

AAG  TAC  CCG  TCG  TGT  GGG  GGC  CTG  CTG  CAG  TCC  CCC  ATA  GAC  CTG  CAC     96
Lys  Tyr  Pro  Ser  Cys  Gly  Gly  Leu  Leu  Gln  Ser  Pro  Ile  Asp  Leu  His
            20                       25                       30

AGT  GAC  ATC  CTC  CAG  TAT  GAC  GCC  AGC  CTC  ACG  CCC  CTC  GAG  TTC  CAA    144
Ser  Asp  Ile  Leu  Gln  Tyr  Asp  Ala  Ser  Leu  Thr  Pro  Leu  Glu  Phe  Gln
        35                       40                       45

GGC  TAC  AAT  CTG  TCT  GCC  AAC  AAG  CAG  TTT  CTC  CTG  ACC  AAC  AAT  GGC    192
Gly  Tyr  Asn  Leu  Ser  Ala  Asn  Lys  Gln  Phe  Leu  Leu  Thr  Asn  Asn  Gly
    50                       55                       60

CAT  TCA  GTG  AAG  CTG  AAC  CTG  CCC  TCG  GAC  ATG  CAC  ATC  CAG  GGC  CTC    240
His  Ser  Val  Lys  Leu  Asn  Leu  Pro  Ser  Asp  Met  His  Ile  Gln  Gly  Leu
65                   70                       75                       80

CAG  TCT  CGC  TAC  AGT  GCC  ACG  CAG  CTG  CAC  CTG  CAC  TGG  GGG  AAC  CCG    288
Gln  Ser  Arg  Tyr  Ser  Ala  Thr  Gln  Leu  His  Leu  His  Trp  Gly  Asn  Pro
                85                       90                       95
```

| | | | | | | | | | | | | | | | | |
|---|---|---|---|---|---|---|---|---|---|---|---|---|---|---|---|---|
| AAT | GAC | CCG | CAC | GGC | TCT | GAG | CAC | ACC | GTC | AGC | GGA | CAG | CAC | TTC | GCC | 336 |
| Asn | Asp | Pro | His | Gly | Ser | Glu | His | Thr | Val | Ser | Gly | Gln | His | Phe | Ala | |
| | | | 100 | | | | 105 | | | | | | 110 | | | |
| GCC | GAG | CTG | CAC | ATT | GTC | CAT | TAT | AAC | TCA | GAC | CTT | TAT | CCT | GAC | GCC | 384 |
| Ala | Glu | Leu | His | Ile | Val | His | Tyr | Asn | Ser | Asp | Leu | Tyr | Pro | Asp | Ala | |
| | | 115 | | | | | 120 | | | | | 125 | | | | |
| AGC | ACT | GCC | AGC | AAC | AAG | TCA | GAA | GGC | CTC | GCT | GTC | CTG | GCT | GTT | CTC | 432 |
| Ser | Thr | Ala | Ser | Asn | Lys | Ser | Glu | Gly | Leu | Ala | Val | Leu | Ala | Val | Leu | |
| | 130 | | | | | 135 | | | | | 140 | | | | | |
| ATT | GAG | ATG | GGC | TCC | TTC | AAT | CCG | TCC | TAT | GAC | AAG | ATC | TTC | AGT | CAC | 480 |
| Ile | Glu | Met | Gly | Ser | Phe | Asn | Pro | Ser | Tyr | Asp | Lys | Ile | Phe | Ser | His | |
| 145 | | | | | 150 | | | | | 155 | | | | | 160 | |
| CTT | CAA | CAT | GTA | AAG | TAC | AAA | GGC | CAG | GAA | GCA | TTC | GTC | CCG | GGA | TTC | 528 |
| Leu | Gln | His | Val | Lys | Tyr | Lys | Gly | Gln | Glu | Ala | Phe | Val | Pro | Gly | Phe | |
| | | | | 165 | | | | | 170 | | | | | 175 | | |
| AAC | ATT | GAA | GAG | CTG | CTT | CCG | GAG | AGG | ACC | GCT | GAA | TAT | TAC | CGC | TAC | 576 |
| Asn | Ile | Glu | Glu | Leu | Leu | Pro | Glu | Arg | Thr | Ala | Glu | Tyr | Tyr | Arg | Tyr | |
| | | | 180 | | | | | 185 | | | | | 190 | | | |
| CGG | GGG | TCC | CTG | ACC | ACA | CCC | CCT | TGC | AAC | CCC | ACT | GTG | CTC | TGG | ACA | 624 |
| Arg | Gly | Ser | Leu | Thr | Thr | Pro | Pro | Cys | Asn | Pro | Thr | Val | Leu | Trp | Thr | |
| | | 195 | | | | | 200 | | | | | 205 | | | | |
| GTT | TTC | CGA | AAC | CCC | GTG | CAA | ATT | TCC | CAG | GAG | CAG | CTG | CTG | GCT | TTG | 672 |
| Val | Phe | Arg | Asn | Pro | Val | Gln | Ile | Ser | Gln | Glu | Gln | Leu | Leu | Ala | Leu | |
| | 210 | | | | | 215 | | | | | 220 | | | | | |
| GAG | ACA | GCC | CTG | TAC | TGC | ACA | CAC | ATG | GAC | GAC | CCT | TCC | CCC | AGA | GAA | 720 |
| Glu | Thr | Ala | Leu | Tyr | Cys | Thr | His | Met | Asp | Asp | Pro | Ser | Pro | Arg | Glu | |
| 225 | | | | | 230 | | | | | 235 | | | | | 240 | |
| ATG | ATC | AAC | AAC | TTC | CGG | CAG | GTC | CAG | AAG | TTC | GAT | GAG | AGG | CTG | GTA | 768 |
| Met | Ile | Asn | Asn | Phe | Arg | Gln | Val | Gln | Lys | Phe | Asp | Glu | Arg | Leu | Val | |
| | | | 245 | | | | | 250 | | | | | 255 | | | |
| TAC | ACC | TCC | TTC | TCC | CAA | GTG | CAA | GTC | TGT | ACT | GCG | GCA | GGA | CTG | | 813 |
| Tyr | Thr | Ser | Phe | Ser | Gln | Val | Gln | Val | Cys | Thr | Ala | Ala | Gly | Leu | | |
| | | | 260 | | | | | 265 | | | | | 270 | | | |

( 2 ) INFORMATION FOR SEQ ID NO:13:

( i ) SEQUENCE CHARACTERISTICS:
        ( A ) LENGTH: 271 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| | | | | | | | | | | | | | | |
|---|---|---|---|---|---|---|---|---|---|---|---|---|---|---|
| Ser | Lys | Trp | Thr | Tyr | Phe | Gly | Pro | Asp | Gly | Glu | Asn | Ser | Trp | Ser | Lys |
| 1 | | | | 5 | | | | | 10 | | | | | 15 | |
| Lys | Tyr | Pro | Ser | Cys | Gly | Gly | Leu | Leu | Gln | Ser | Pro | Ile | Asp | Leu | His |
| | | | 20 | | | | | 25 | | | | | 30 | | |
| Ser | Asp | Ile | Leu | Gln | Tyr | Asp | Ala | Ser | Leu | Thr | Pro | Leu | Glu | Phe | Gln |
| | | | 35 | | | | 40 | | | | | 45 | | | |
| Gly | Tyr | Asn | Leu | Ser | Ala | Asn | Lys | Gln | Phe | Leu | Leu | Thr | Asn | Asn | Gly |
| | | 50 | | | | | 55 | | | | | 60 | | | |
| His | Ser | Val | Lys | Leu | Asn | Leu | Pro | Ser | Asp | Met | His | Ile | Gln | Gly | Leu |
| 65 | | | | | 70 | | | | | 75 | | | | | 80 |
| Gln | Ser | Arg | Tyr | Ser | Ala | Thr | Gln | Leu | His | Leu | His | Trp | Gly | Asn | Pro |
| | | | | 85 | | | | | 90 | | | | | 95 | |
| Asn | Asp | Pro | His | Gly | Ser | Glu | His | Thr | Val | Ser | Gly | Gln | His | Phe | Ala |
| | | | 100 | | | | 105 | | | | | 110 | | | |
| Ala | Glu | Leu | His | Ile | Val | His | Tyr | Asn | Ser | Asp | Leu | Tyr | Pro | Asp | Ala |
| | | 115 | | | | | 120 | | | | | 125 | | | |

```
Ser  Thr  Ala  Ser  Asn  Lys  Ser  Glu  Gly  Leu  Ala  Val  Leu  Ala  Val  Leu
     130                 135                 140

Ile  Glu  Met  Gly  Ser  Phe  Asn  Pro  Ser  Tyr  Asp  Lys  Ile  Phe  Ser  His
145                      150                 155                           160

Leu  Gln  His  Val  Lys  Tyr  Lys  Gly  Gln  Ala  Phe  Val  Pro  Gly  Phe
                    165                      170                 175

Asn  Ile  Glu  Glu  Leu  Leu  Pro  Glu  Arg  Thr  Ala  Glu  Tyr  Tyr  Arg  Tyr
               180                      185                      190

Arg  Gly  Ser  Leu  Thr  Thr  Pro  Pro  Cys  Asn  Pro  Thr  Val  Leu  Trp  Thr
          195                      200                 205

Val  Phe  Arg  Asn  Pro  Val  Gln  Ile  Ser  Gln  Glu  Gln  Leu  Leu  Ala  Leu
     210                      215                 220

Glu  Thr  Ala  Leu  Tyr  Cys  Thr  His  Met  Asp  Asp  Pro  Ser  Pro  Arg  Glu
225                      230                 235                           240

Met  Ile  Asn  Asn  Phe  Arg  Gln  Val  Gln  Lys  Phe  Asp  Glu  Arg  Leu  Val
                    245                      250                      255

Tyr  Thr  Ser  Phe  Ser  Gln  Val  Gln  Val  Cys  Thr  Ala  Ala  Gly  Leu
                    260                      265                 270
```

( 2 ) INFORMATION FOR SEQ ID NO:14:

( i ) SEQUENCE CHARACTERISTICS:
        ( A ) LENGTH: 822 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..822

( x i ) SEQUENCE DESCRIPTION: SEQ ID NO:14:

```
TCC  AAG  TGG  ACT  TAT  TTT  GGT  CCT  GAT  GGG  GAG  AAT  AGC  TGG  TCC  AAG       48
Ser  Lys  Trp  Thr  Tyr  Phe  Gly  Pro  Asp  Gly  Glu  Asn  Ser  Trp  Ser  Lys
 1                       5                        10                      15

AAG  TAC  CCG  TCG  TGT  GGG  GGC  CTG  CTG  CAG  TCC  CCC  ATA  GAC  CTG  CAC       96
Lys  Tyr  Pro  Ser  Cys  Gly  Gly  Leu  Leu  Gln  Ser  Pro  Ile  Asp  Leu  His
                    20                       25                       30

AGT  GAC  ATC  CTC  CAG  TAT  GAC  GCC  AGC  CTC  ACG  CCC  CTC  GAG  TTC  CAA      144
Ser  Asp  Ile  Leu  Gln  Tyr  Asp  Ala  Ser  Leu  Thr  Pro  Leu  Glu  Phe  Gln
               35                       40                       45

GGC  TAC  AAT  CTG  TCT  GCC  AAC  AAG  CAG  TTT  CTC  CTG  ACC  AAC  AAT  GGC      192
Gly  Tyr  Asn  Leu  Ser  Ala  Asn  Lys  Gln  Phe  Leu  Leu  Thr  Asn  Asn  Gly
          50                       55                       60

CAT  TCA  GTG  AAG  CTG  AAC  CTG  CCC  TCG  GAC  ATG  CAC  ATC  CAG  GGC  CTC      240
His  Ser  Val  Lys  Leu  Asn  Leu  Pro  Ser  Asp  Met  His  Ile  Gln  Gly  Leu
 65                      70                       75                            80

CAG  TCT  CGC  TAC  AGT  GCC  ACG  CAG  CTG  CAC  CTG  CAC  TGG  GGG  AAC  CCG      288
Gln  Ser  Arg  Tyr  Ser  Ala  Thr  Gln  Leu  His  Leu  His  Trp  Gly  Asn  Pro
                    85                       90                       95

AAT  GAC  CCG  CAC  GGC  TCT  GAG  CAC  ACC  GTC  AGC  GGA  CAG  CAC  TTC  GCC      336
Asn  Asp  Pro  His  Gly  Ser  Glu  His  Thr  Val  Ser  Gly  Gln  His  Phe  Ala
               100                      105                      110

GCC  GAG  CTG  CAC  ATT  GTC  CAT  TAT  AAC  TCA  GAC  CTT  TAT  CCT  GAC  GCC      384
Ala  Glu  Leu  His  Ile  Val  His  Tyr  Asn  Ser  Asp  Leu  Tyr  Pro  Asp  Ala
          115                      120                      125

AGC  ACT  GCC  AGC  AAC  AAG  TCA  GAA  GGC  CTC  GCT  GTC  CTG  GCT  GTT  CTC      432
Ser  Thr  Ala  Ser  Asn  Lys  Ser  Glu  Gly  Leu  Ala  Val  Leu  Ala  Val  Leu
     130                 135                      140
```

```
ATT GAG ATG GGC TCC TTC AAT CCG TCC TAT GAC AAG ATC TTC AGT CAC        480
Ile Glu Met Gly Ser Phe Asn Pro Ser Tyr Asp Lys Ile Phe Ser His
145                 150                 155                 160

CTT CAA CAT GTA AAG TAC AAA GGC CAG GAA GCA TTC GTC CCG GGA TTC        528
Leu Gln His Val Lys Tyr Lys Gly Gln Glu Ala Phe Val Pro Gly Phe
                165                 170                 175

AAC ATT GAA GAG CTG CTT CCG GAG AGG ACC GCT GAA TAT TAC CGC TAC        576
Asn Ile Glu Glu Leu Leu Pro Glu Arg Thr Ala Glu Tyr Tyr Arg Tyr
            180                 185                 190

CGG GGG TCC CTG ACC ACA CCC CCT TGC AAC CCC ACT GTG CTC TGG ACA        624
Arg Gly Ser Leu Thr Thr Pro Pro Cys Asn Pro Thr Val Leu Trp Thr
        195                 200                 205

GTT TTC CGA AAC CCC GTG CAA ATT TCC CAG GAG CAG CTG CTG GCT TTG        672
Val Phe Arg Asn Pro Val Gln Ile Ser Gln Glu Gln Leu Leu Ala Leu
    210                 215                 220

GAG ACA GCC CTG TAC TGC ACA CAC ATG GAC GAC CCT TCC CCC AGA GAA        720
Glu Thr Ala Leu Tyr Cys Thr His Met Asp Asp Pro Ser Pro Arg Glu
225                 230                 235                 240

ATG ATC AAC AAC TTC CGG CAG GTC CAG AAG TTC GAT GAG AGG CTG GTA        768
Met Ile Asn Asn Phe Arg Gln Val Gln Lys Phe Asp Glu Arg Leu Val
                245                 250                 255

TAC ACC TCC TTC TCC CAA GTG CAA GTC TGT ACT GCG GCA GGA CTG AGT        816
Tyr Thr Ser Phe Ser Gln Val Gln Val Cys Thr Ala Ala Gly Leu Ser
                260                 265                 270

CTG GGC                                                                 822
Leu Gly
```

(2) INFORMATION FOR SEQ ID NO:15:

(i) SEQUENCE CHARACTERISTICS:
        (A) LENGTH: 274 amino acids
        (B) TYPE: amino acid
        (D) TOPOLOGY: linear (ii) MOLECULE TYPE: protein (xi) SEQUENCE DESCRIPTION: SEQ ID NO:15:

```
Ser Lys Trp Thr Tyr Phe Gly Pro Asp Gly Glu Asn Ser Trp Ser Lys
1               5                   10                  15

Lys Tyr Pro Ser Cys Gly Gly Leu Leu Gln Ser Pro Ile Asp Leu His
                20                  25                  30

Ser Asp Ile Leu Gln Tyr Asp Ala Ser Leu Thr Pro Leu Glu Phe Gln
            35                  40                  45

Gly Tyr Asn Leu Ser Ala Asn Lys Gln Phe Leu Leu Thr Asn Asn Gly
        50                  55                  60

His Ser Val Lys Leu Asn Leu Pro Ser Asp Met His Ile Gln Gly Leu
65                  70                  75                  80

Gln Ser Arg Tyr Ser Ala Thr Gln Leu His Leu His Trp Gly Asn Pro
                85                  90                  95

Asn Asp Pro His Gly Ser Glu His Thr Val Ser Gly Gln His Phe Ala
                100                 105                 110

Ala Glu Leu His Ile Val His Tyr Asn Ser Asp Leu Tyr Pro Asp Ala
            115                 120                 125

Ser Thr Ala Ser Asn Lys Ser Glu Gly Leu Ala Val Leu Ala Val Leu
        130                 135                 140

Ile Glu Met Gly Ser Phe Asn Pro Ser Tyr Asp Lys Ile Phe Ser His
145                 150                 155                 160

Leu Gln His Val Lys Tyr Lys Gly Gln Glu Ala Phe Val Pro Gly Phe
                165                 170                 175
```

| Asn | Ile | Glu | Glu<br>180 | Leu | Leu | Pro | Glu<br>185 | Arg | Thr | Ala | Glu | Tyr<br>190 | Tyr | Arg | Tyr |
|---|---|---|---|---|---|---|---|---|---|---|---|---|---|---|---|
| Arg | Gly | Ser<br>195 | Leu | Thr | Thr | Pro | Pro<br>200 | Cys | Asn | Pro | Thr | Val<br>205 | Leu | Trp | Thr |
| Val | Phe<br>210 | Arg | Asn | Pro | Val | Gln<br>215 | Ile | Ser | Gln | Glu | Gln<br>220 | Leu | Leu | Ala | Leu |
| Glu<br>225 | Thr | Ala | Leu | Tyr | Cys<br>230 | Thr | His | Met | Asp | Asp<br>235 | Pro | Ser | Pro | Arg | Glu<br>240 |
| Met | Ile | Asn | Asn | Phe<br>245 | Arg | Gln | Val | Gln | Lys<br>250 | Phe | Asp | Glu | Arg | Leu<br>255 | Val |
| Tyr | Thr | Ser | Phe<br>260 | Ser | Gln | Val | Gln | Val<br>265 | Cys | Thr | Ala | Ala | Gly<br>270 | Leu | Ser |
| Leu | Gly | | | | | | | | | | | | | | |

( 2 ) INFORMATION FOR SEQ ID NO:16:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:16:

CTTTTTTGAT ACCCTTCCTT CTGAA        25

( 2 ) INFORMATION FOR SEQ ID NO:17:

( i ) SEQUENCE CHARACTERISTICS:
        ( A ) LENGTH: 986 base pairs
        ( B ) TYPE: nucleic acid
        ( C ) STRANDEDNESS: both
        ( D ) TOPOLOGY: linear ( i i ) MOLECULE TYPE: cDNA ( i x ) FEATURE:
        ( A ) NAME/KEY: CDS
        ( B ) LOCATION: 1..975

( x i ) SEQUENCE DESCRIPTION: SEQ ID NO:17:

| TCC | AAG | TGG | ACT | TAT | TTT | GGT | CCT | GAT | GGG | GAG | AAT | AGC | TGG | TCC | AAG | 48 |
|---|---|---|---|---|---|---|---|---|---|---|---|---|---|---|---|---|
| Ser<br>1 | Lys | Trp | Thr | Tyr<br>5 | Phe | Gly | Pro | Asp | Gly<br>10 | Glu | Asn | Ser | Trp | Ser<br>15 | Lys | |
| AAG | TAC | CCG | TCG | TGT | GGG | GGC | CTG | CTG | CAG | TCC | CCC | ATA | GAC | CTG | CAC | 96 |
| Lys | Tyr | Pro | Ser<br>20 | Cys | Gly | Gly | Leu | Leu<br>25 | Gln | Ser | Pro | Ile | Asp<br>30 | Leu | His | |
| AGT | GAC | ATC | CTC | CAG | TAT | GAC | GCC | AGC | CTC | ACG | CCC | CTC | GAG | TTC | CAA | 144 |
| Ser | Asp | Ile<br>35 | Leu | Gln | Tyr | Asp | Ala<br>40 | Ser | Leu | Thr | Pro | Leu<br>45 | Glu | Phe | Gln | |
| GGC | TAC | AAT | CTG | TCT | GCC | AAC | AAG | CAG | TTT | CTC | CTG | ACC | AAC | AAT | GGC | 192 |
| Gly | Tyr<br>50 | Asn | Leu | Ser | Ala | Asn<br>55 | Lys | Gln | Phe | Leu | Leu<br>60 | Thr | Asn | Asn | Gly | |
| CAT | TCA | GTG | AAG | CTG | AAC | CTG | CCC | TCG | GAC | ATG | CAC | ATC | CAG | GGC | CTC | 240 |
| His<br>65 | Ser | Val | Lys | Leu<br>70 | Asn | Leu | Pro | Ser<br>75 | Asp | Met | His | Ile | Gln<br>80 | Gly | Leu | |
| CAG | TCT | CGC | TAC | AGT | GCC | ACG | CAG | CTG | CAC | CTG | CAC | TGG | GGG | AAC | CCG | 288 |
| Gln | Ser | Arg | Tyr<br>85 | Ser | Ala | Thr | Gln | Leu<br>90 | His | Leu | His | Trp | Gly<br>95 | Asn | Pro | |

| | | | | | | | | | | | | | | | | |
|---|---|---|---|---|---|---|---|---|---|---|---|---|---|---|---|---|
| AAT | GAC | CCG | CAC | GGC | TCT | GAG | CAC | ACC | GTC | AGC | GGA | CAG | CAC | TTC | GCC | 336 |
| Asn | Asp | Pro | His | Gly | Ser | Glu | His | Thr | Val | Ser | Gly | Gln | His | Phe | Ala | |
| | | | 100 | | | | 105 | | | | | | 110 | | | |
| GCC | GAG | CTG | CAC | ATT | GTC | CAT | TAT | AAC | TCA | GAC | CTT | TAT | CCT | GAC | GCC | 384 |
| Ala | Glu | Leu | His | Ile | Val | His | Tyr | Asn | Ser | Asp | Leu | Tyr | Pro | Asp | Ala | |
| | | | 115 | | | | 120 | | | | | 125 | | | | |
| AGC | ACT | GCC | AGC | AAC | AAG | TCA | GAA | GGC | CTC | GCT | GTC | CTG | GCT | GTT | CTC | 432 |
| Ser | Thr | Ala | Ser | Asn | Lys | Ser | Glu | Gly | Leu | Ala | Val | Leu | Ala | Val | Leu | |
| | 130 | | | | | 135 | | | | | 140 | | | | | |
| ATT | GAG | ATG | GGC | TCC | TTC | AAT | CCG | TCC | TAT | GAC | AAG | ATC | TTC | AGT | CAC | 480 |
| Ile | Glu | Met | Gly | Ser | Phe | Asn | Pro | Ser | Tyr | Asp | Lys | Ile | Phe | Ser | His | |
| 145 | | | | | 150 | | | | | 155 | | | | | 160 | |
| CTT | CAA | CAT | GTA | AAG | TAC | AAA | GGC | CAG | GAA | GCA | TTC | GTC | CCG | GGA | TTC | 528 |
| Leu | Gln | His | Val | Lys | Tyr | Lys | Gly | Gln | Glu | Ala | Phe | Val | Pro | Gly | Phe | |
| | | | | 165 | | | | | 170 | | | | | 175 | | |
| AAC | ATT | GAA | GAG | CTG | CTT | CCG | GAG | AGG | ACC | GCT | GAA | TAT | TAC | CGC | TAC | 576 |
| Asn | Ile | Glu | Glu | Leu | Leu | Pro | Glu | Arg | Thr | Ala | Glu | Tyr | Tyr | Arg | Tyr | |
| | | | 180 | | | | | 185 | | | | | 190 | | | |
| CGG | GGG | TCC | CTG | ACC | ACA | CCC | CCT | TGC | AAC | CCC | ACT | GTG | CTC | TGG | ACA | 624 |
| Arg | Gly | Ser | Leu | Thr | Thr | Pro | Pro | Cys | Asn | Pro | Thr | Val | Leu | Trp | Thr | |
| | | 195 | | | | | 200 | | | | | 205 | | | | |
| GTT | TTC | CGA | AAC | CCC | GTG | CAA | ATT | TCC | CAG | GAG | CAG | CTG | CTG | GCT | TTG | 672 |
| Val | Phe | Arg | Asn | Pro | Val | Gln | Ile | Ser | Gln | Glu | Gln | Leu | Leu | Ala | Leu | |
| | 210 | | | | | 215 | | | | | 220 | | | | | |
| GAG | ACA | GCC | CTG | TAC | TGC | ACA | CAC | ATG | GAC | GAC | CCT | TCC | CCC | AGA | GAA | 720 |
| Glu | Thr | Ala | Leu | Tyr | Cys | Thr | His | Met | Asp | Asp | Pro | Ser | Pro | Arg | Glu | |
| 225 | | | | | 230 | | | | | 235 | | | | | 240 | |
| ATG | ATC | AAC | AAC | TTC | CGG | CAG | GTC | CAG | AAG | TTC | GAT | GAG | AGG | CTG | GTA | 768 |
| Met | Ile | Asn | Asn | Phe | Arg | Gln | Val | Gln | Lys | Phe | Asp | Glu | Arg | Leu | Val | |
| | | | 245 | | | | | 250 | | | | | 255 | | | |
| TAC | ACC | TCC | TTC | TCC | CAA | GTG | CAA | GTC | TGT | ACT | GCG | GCA | GGA | CTG | AGT | 816 |
| Tyr | Thr | Ser | Phe | Ser | Gln | Val | Gln | Val | Cys | Thr | Ala | Ala | Gly | Leu | Ser | |
| | | | 260 | | | | | 265 | | | | | 270 | | | |
| CTG | GGC | ATC | ATC | CTC | TCA | CTG | GCC | CTG | GCT | GGC | ATT | CTT | GGC | ATC | TGT | 864 |
| Leu | Gly | Ile | Ile | Leu | Ser | Leu | Ala | Leu | Ala | Gly | Ile | Leu | Gly | Ile | Cys | |
| | | 275 | | | | | 280 | | | | | 280 | | | | |
| ATT | GTG | GTG | GTG | GTG | TCC | ATT | TGG | CTT | TTC | AGA | AGG | AAG | GGT | ATC | AAA | 912 |
| Ile | Val | Val | Val | Val | Ser | Ile | Trp | Leu | Phe | Arg | Arg | Lys | Gly | Ile | Lys | |
| | 290 | | | | | 295 | | | | | 300 | | | | | |
| AAA | GGT | GAT | AAC | AAG | GGA | GTC | ATT | TAC | AAG | CCA | GCC | ACC | AAG | ATG | GAG | 960 |
| Lys | Gly | Asp | Asn | Lys | Gly | Val | Ile | Tyr | Lys | Pro | Ala | Thr | Lys | Met | Glu | |
| 305 | | | | | 310 | | | | | 315 | | | | | 320 | |
| ACT | GAG | GCC | CAC | GCT | TGAGGTCCCC G | | | | | | | | | | | 986 |
| Thr | Glu | Ala | His | Ala | | | | | | | | | | | | |
| | | | | 325 | | | | | | | | | | | | |

( 2 ) INFORMATION FOR SEQ ID NO:18:

( i ) SEQUENCE CHARACTERISTICS:
        ( A ) LENGTH: 325 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

| Ser | Lys | Trp | Thr | Tyr | Phe | Gly | Pro | Asp | Gly | Glu | Asn | Ser | Trp | Ser | Lys |
|---|---|---|---|---|---|---|---|---|---|---|---|---|---|---|---|
| 1 | | | | 5 | | | | | 10 | | | | | 15 | |

| Lys | Tyr | Pro | Ser | Cys | Gly | Gly | Leu | Leu | Gln | Ser | Pro | Ile | Asp | Leu | His |
|---|---|---|---|---|---|---|---|---|---|---|---|---|---|---|---|
| | | | 20 | | | | | 25 | | | | | 30 | | |

Ser Asp Ile Leu Gln Tyr Asp Ala Ser Leu Thr Pro Leu Glu Phe Gln

|     |     | 35  |     |     |     |     | 40  |     |     |     |     | 45  |     |     |
|-----|-----|-----|-----|-----|-----|-----|-----|-----|-----|-----|-----|-----|-----|-----|
| Gly | Tyr | Asn | Leu | Ser | Ala | Asn | Lys | Gln | Phe | Leu | Leu | Thr | Asn | Asn | Gly |
|     | 50  |     |     |     |     | 55  |     |     |     |     | 60  |     |     |     |     |
| His | Ser | Val | Lys | Leu | Asn | Leu | Pro | Ser | Asp | Met | His | Ile | Gln | Gly | Leu |
| 65  |     |     |     |     | 70  |     |     |     |     | 75  |     |     |     |     | 80  |
| Gln | Ser | Arg | Tyr | Ser | Ala | Thr | Gln | Leu | His | Leu | His | Trp | Gly | Asn | Pro |
|     |     |     |     | 85  |     |     |     |     |     | 90  |     |     |     |     | 95  |
| Asn | Asp | Pro | His | Gly | Ser | Glu | His | Thr | Val | Ser | Gly | Gln | His | Phe | Ala |
|     |     |     | 100 |     |     |     |     | 105 |     |     |     |     | 110 |     |     |
| Ala | Glu | Leu | His | Ile | Val | His | Tyr | Asn | Ser | Asp | Leu | Tyr | Pro | Asp | Ala |
|     |     | 115 |     |     |     |     | 120 |     |     |     |     | 125 |     |     |     |
| Ser | Thr | Ala | Ser | Asn | Lys | Ser | Glu | Gly | Leu | Ala | Val | Leu | Ala | Val | Leu |
|     | 130 |     |     |     |     | 135 |     |     |     |     | 140 |     |     |     |     |
| Ile | Glu | Met | Gly | Ser | Phe | Asn | Pro | Ser | Tyr | Asp | Lys | Ile | Phe | Ser | His |
| 145 |     |     |     |     | 150 |     |     |     |     | 155 |     |     |     |     | 160 |
| Leu | Gln | His | Val | Lys | Tyr | Lys | Gly | Gln | Glu | Ala | Phe | Val | Pro | Gly | Phe |
|     |     |     |     | 165 |     |     |     |     | 170 |     |     |     |     | 175 |     |
| Asn | Ile | Glu | Glu | Leu | Leu | Pro | Glu | Arg | Thr | Ala | Glu | Tyr | Tyr | Arg | Tyr |
|     |     |     | 180 |     |     |     |     | 185 |     |     |     |     | 190 |     |     |
| Arg | Gly | Ser | Leu | Thr | Thr | Pro | Pro | Cys | Asn | Pro | Thr | Val | Leu | Trp | Thr |
|     |     | 195 |     |     |     |     | 200 |     |     |     |     | 205 |     |     |     |
| Val | Phe | Arg | Asn | Pro | Val | Gln | Ile | Ser | Gln | Glu | Gln | Leu | Leu | Ala | Leu |
|     | 210 |     |     |     |     | 215 |     |     |     |     | 220 |     |     |     |     |
| Glu | Thr | Ala | Leu | Tyr | Cys | Thr | His | Met | Asp | Pro | Ser | Pro | Arg | Glu |
| 225 |     |     |     |     | 230 |     |     |     |     | 235 |     |     |     |     | 240 |
| Met | Ile | Asn | Asn | Phe | Arg | Gln | Val | Gln | Lys | Phe | Asp | Glu | Arg | Leu | Val |
|     |     |     |     | 245 |     |     |     |     | 250 |     |     |     |     | 255 |     |
| Tyr | Thr | Ser | Phe | Ser | Gln | Val | Gln | Val | Cys | Thr | Ala | Ala | Gly | Leu | Ser |
|     |     |     | 260 |     |     |     |     | 265 |     |     |     |     | 270 |     |     |
| Leu | Gly | Ile | Ile | Leu | Ser | Leu | Ala | Leu | Ala | Gly | Ile | Leu | Gly | Ile | Cys |
|     |     | 275 |     |     |     |     | 280 |     |     |     |     | 285 |     |     |     |
| Ile | Val | Val | Val | Val | Ser | Ile | Trp | Leu | Phe | Arg | Arg | Lys | Gly | Ile | Lys |
|     | 290 |     |     |     |     | 295 |     |     |     |     | 300 |     |     |     |     |
| Lys | Gly | Asp | Asn | Lys | Gly | Val | Ile | Tyr | Lys | Pro | Ala | Thr | Lys | Met | Glu |
| 305 |     |     |     |     | 310 |     |     |     |     | 315 |     |     |     |     | 320 |
| Thr | Glu | Ala | His | Ala |
|     |     |     |     | 325 |

( 2 ) INFORMATION FOR SEQ ID NO:19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:19:

ACATTGAAGA GCTGCTTCCG G          21

( 2 ) INFORMATION FOR SEQ ID NO:20:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:20:

| AATTTGCACG GGGTTTCGG | | | | | 19 |
|---|---|---|---|---|---|

( 2 ) INFORMATION FOR SEQ ID NO:21:

( i ) SEQUENCE CHARACTERISTICS:
        ( A ) LENGTH: 1363 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:21:

| CTGACACCAC | TCAGACCGTG | TGTGATCTGG | CTCAACCAGT | TCTGCGATCC | CACCCAGGAA | 60 |
|---|---|---|---|---|---|---|
| CAGAAGACTG | CAAGAAAACG | TTACTTCAAC | CCCCCTGTGA | TCCCATCTGC | AACCTGACCA | 120 |
| ATCAGCACTC | CCCAAGTCCC | AAGCCCCTAT | CTGCCAAATT | ATCTTAAAA | ACTCCCCAGA | 180 |
| GGCAGGGTGC | AGTGGTTCAA | CGCCTGTAAT | CCCAGCACTT | TAGGTGGATC | ACGAGATCAA | 240 |
| GAGATCAAGA | CCAGCCTGGC | CAACATGGTG | AAACCCCGTC | TTCTTACTAA | AAATACAAAA | 300 |
| ATTAGCTGGG | TGTGGCGGCG | CGTGCCTGTA | ATCCAGCTA | CCCAGGAGGC | TGAGGCAGGA | 360 |
| GAATCGCTTG | AACCCGTGAG | GCAGAGGTTG | CAGTGAGCCA | AGACCATGCC | ACTGCATTTC | 420 |
| AGCCTGGGCG | ACAGAGGGGA | ACTCCGTCTG | AACAAACAAA | CAAACAAACA | ACTCCCGGAA | 480 |
| TGCTTGGGGA | GACTGATTTG | AGTACTGGAA | TCCAGTACT | TTAGGAGGCC | AAGGTAGGTG | 540 |
| GATCATTTGA | GGTCAGGAGT | TCCAGACCAG | CCTGGCCAAC | ATGGTGAAAC | CCCGTCTCTA | 600 |
| CTAAAATTAG | AAAAATTAGC | CGGGTGTGGT | GGTGGGCGCC | TGTAATCCCA | GCACTTTGGG | 660 |
| AAGCCAAGGC | AGGTGAATTA | TCTGAGGTCG | GGAGTTTAAG | GCCAGCCTTA | AACTGGCGAA | 720 |
| ACCCCGCCTC | TACTAAAAAT | ACAAAATTA | TCTGGGCATG | GTGGCATGTG | CCTGTAATCC | 780 |
| CAGCTACTCG | GGAGGCTGAG | GCAGGAGAAT | CGCTTGAACC | CGGGAGGCGG | AGGTTGCAGT | 840 |
| GAGCCGAGAT | CACGCTATTG | CACTCCGGCC | TGGGCAACAG | AGCGAGACTC | CGTCTCAAAC | 900 |
| AAACAAACAA | AGGAACGAAA | ACTCCGGTCT | CCGGCACGGC | AAGCTCTGCG | TGAATTACTT | 960 |
| TCTCCATTGC | AACTCCCCTG | TCTTGATAAA | TGGGCTCTGT | CTAAGCAGCG | GGCAAGGTGA | 1020 |
| ACTCGTTGGG | CTGTTACAGG | ACCAGTGACA | GACCAAGGCA | TGCCACTGAA | GGAATCCCTA | 1080 |
| GACGCACCCT | TCTGGATGTG | AGGCAGGCGG | ATCTCACCCC | ACGCCTGCCA | GCAGCTCCTC | 1140 |
| GGAGAACTGT | GTTCCTGGGT | CAGCCCTGGC | CCAGAGGAGC | GCCGGGACC | CGCAGAGTGC | 1200 |
| TGCTGAAGTC | AAGGCTACAA | CTCACCTAGG | ATCTGGGGCG | CCAGCCTCCG | GTGGGCAGGG | 1260 |
| CGTTCTCCTC | CCCCACCCCC | TCCCCGCACG | ATGACATCAA | GTGTTTGGCG | TTGAGTTGCT | 1320 |
| CCATAAAAGC | TGCCCGGGGA | AGCCAGGAGA | GCGAAGGGCG | GAC | | 1363 |

( 2 ) INFORMATION FOR SEQ ID NO:22:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO (x i) SEQUENCE DESCRIPTION: SEQ ID NO:22:

GTCCACTTGG ATCCGTTCAC TGG                                    23